(12) United States Patent
Takeichi et al.

(10) Patent No.: US 11,182,599 B2
(45) Date of Patent: Nov. 23, 2021

(54) MOTION STATE EVALUATION SYSTEM, MOTION STATE EVALUATION DEVICE, MOTION STATE EVALUATION SERVER, MOTION STATE EVALUATION METHOD, AND MOTION STATE EVALUATION PROGRAM

(71) Applicant: ASICS CORPORATION, Kobe (JP)

(72) Inventors: Kazunari Takeichi, Kobe (JP); Takehiro Tagawa, Kobe (JP); Ryota Shinayama, Kobe (JP)

(73) Assignee: ASICS CORPORATION, Kobe (JP)

( * ) Notice: Subject to any disclaimer, the term of this patent is extended or adjusted under 35 U.S.C. 154(b) by 0 days.

(21) Appl. No.: 16/858,226

(22) Filed: Apr. 24, 2020

(65) Prior Publication Data

US 2020/0250408 A1  Aug. 6, 2020

Related U.S. Application Data

(63) Continuation of application No. PCT/JP2017/038909, filed on Oct. 27, 2017.

(51) Int. Cl.
*G06K 9/00* (2006.01)
*G06K 9/46* (2006.01)
*G06T 7/20* (2017.01)

(52) U.S. Cl.
CPC ..... *G06K 9/00348* (2013.01); *G06K 9/00369* (2013.01); *G06K 9/46* (2013.01); *G06T 7/20* (2013.01); *G06T 2207/30196* (2013.01)

(58) Field of Classification Search
CPC .. G06K 9/00348; G06K 9/00369; G06K 9/46; G06T 7/20
See application file for complete search history.

(56) References Cited

U.S. PATENT DOCUMENTS

2005/0232467 A1  10/2005  Mohri et al.
2011/0022349 A1   1/2011  Stirling et al.
(Continued)

FOREIGN PATENT DOCUMENTS

CN  106027796 A  10/2016
CN  106709663 A   5/2017
(Continued)

OTHER PUBLICATIONS

International Search Report issued in PCT/JP2017/038909; dated Jan. 30, 2018.
(Continued)

*Primary Examiner* — Md K Talukder
(74) *Attorney, Agent, or Firm* — Studebaker & Brackett PC

(57) ABSTRACT

A motion state evaluation system is provided with a motion analyzer obtains a value representing a motion state of the subject based on a ratio, to a reference length, of a distance between predetermined joints estimated on an image; a reference storage stores a height of a subject as the reference length; a motion analyzer obtains, as a value for use in evaluation of motion of the subject, the value representing the motion state of the subject from a feature point distance on the image of a plurality of anatomical feature points based on a ratio, to the height, of a distance on the image that is determined from the plurality of anatomical feature points and corresponds to the height of the subject; and an evaluation processor evaluates the motion of the subject based on the value representing the motion state.

18 Claims, 16 Drawing Sheets

(56) References Cited

U.S. PATENT DOCUMENTS

| | | | |
|---|---|---|---|
| 2013/0028517 A1* | 1/2013 | Yoo | G06K 9/00375 |
| | | | 382/173 |
| 2013/0243259 A1* | 9/2013 | Kawaguchi | G06K 9/3241 |
| | | | 382/103 |
| 2016/0030804 A1* | 2/2016 | Mizuochi | A61B 5/11 |
| | | | 482/8 |
| 2018/0200598 A1 | 7/2018 | Guan et al. | |
| 2019/0362139 A1* | 11/2019 | Mehl | A61B 5/1116 |
| 2020/0089958 A1* | 3/2020 | Zhu | G06K 9/00369 |
| 2020/0222757 A1* | 7/2020 | Yang | G09B 5/06 |
| 2020/0250408 A1* | 8/2020 | Takeichi | G06K 9/00369 |
| 2020/0297243 A1* | 9/2020 | Katsuhara | A61B 5/0024 |
| 2020/0320297 A1* | 10/2020 | Ahn | G06F 3/0482 |

FOREIGN PATENT DOCUMENTS

| | | |
|---|---|---|
| EP | 2695645 A1 | 2/2014 |
| JP | WO2013/129606 A1 | 7/2015 |
| JP | 2017-077403 A | 4/2017 |

OTHER PUBLICATIONS

International Preliminary Report on Patentability issued in PCT/JP2017/038909; completed Oct. 2, 2019.

Alexander Toshev et al.; "DeepPose: Human Pose Estimation via Deep Neural Networks"; Aug. 20, 2014; pp. 1-9. arXiv:1312.4659v3 [cs.CV].

Shih-En Wei et al.; "Convolutional Pose Machines"; Apr. 12, 2016; pp. 1-9. arXiv:1602.00134v4 [cs.CV].

Zhe Cao et al.; "Realtime Multi-Person 2D Pose Estimation using Part Affinity Fields"; Apr. 14, 2017; pp. 1-9. arXiv:1611.08050v2 [cs.CV].

Yi Yang et al.; "Articulated Human Detection with Flexible Mixtures-of-Parts"; Dec. 2013; pp. 1-15.

An Office Action mailed by the Indian Patent Office dated Jul. 9, 2021, which corresponds to Indian Patent Application 202017020559 and is related to U.S. Appl. No. 16/858,226.

The extended European search report issued by the European Patent Office dated May 20, 2021, which corresponds to European Patent Application No. 17929623.1-1210 and is related to U.S. Appl. No. 16/858,226.

* cited by examiner

FIG. 9

| PATTERN | FORM | RECOMMENDED TRAINING CONTENTS |
|---|---|---|
| 1 | STEP LENGTH SMALL | TRAINING No. 1 |
| 2 | BODY POSTURE LARGE | TRAINING No. 2 |
| 3 | VERTICAL MOTION LARGE | TRAINING No. 3 |
| 4 | ARM SWING WIDTH SMALL | TRAINING No. 4 |

| PATTERN | MARATHON TIME (h) | NORMAL PACE (min/km) | FORM | RECOMMENDED SHOES |
|---|---|---|---|---|
| 1 | ~2.5 | ~4 | LONG STEP LENGTH TYPE | SMR4 |
| 2 | | | HIGH STEP FREQUENCY TYPE | SJS |
| 3 | 2.5~3.0 | 4~4.5 | LONG STEP LENGTH TYPE | TZ5 |
| 4 | | | HIGH STEP FREQUENCY TYPE | SSG4 |
| 5 | 3.0~3.5 | 4.5~5.0 | LONG STEP LENGTH TYPE | GR11 |
| 6 | | | HIGH STEP FREQUENCY TYPE | GR11 |
| 7 | 3.5~4.0 | 5.0~5.5 | LONG STEP LENGTH TYPE | GT22 |
| 8 | | | HIGH STEP FREQUENCY TYPE | GF4 |
| 9 | 4.0~4.5 | 5.5~6.0 | OVERPRONATION | NF |
| 10 | | | UNDERPRONATION | DF |
| 11 | 4.5~ | 6.0~ | OVERPRONATION | GK24 |
| 12 | | | UNDERPRONATION | GN19 |

260

MOTION STATE EVALUATION SYSTEM, MOTION STATE EVALUATION DEVICE, MOTION STATE EVALUATION SERVER, MOTION STATE EVALUATION METHOD, AND MOTION STATE EVALUATION PROGRAM

BACKGROUND OF THE INVENTION

1. Field of the Invention

The present invention relates to a motion form analysis system. In particular, the present invention relates to a system configured to analyze a form of a subject during exercise.

2. Description of the Related Art

In the conventional practice, as a system configured to automatically diagnose a running form, a technique for analyzing a running form by recognizing positions of a plurality of markers attached to a body of a runner from a moving image of the runner is known (for example, see patent documents 1 and 2).

[patent literature 1] WO 2013-129606 A1
[patent literature 2] JP 2017-77403 A

Under such a conventional motion form analysis technique, it is not possible to conduct accurate analysis without an expensive special camera or a dedicated sensor, preventing an individual from easily conducting analysis.

SUMMARY OF THE INVENTION

The present invention has been made in view of such circumstances, and it is therefore an object of the present invention to provide a system capable of conducting image-analysis on a motion form in response to a simple operation made by a user.

In order to solve the above problems, a motion state evaluation system according to one embodiment of the present invention includes an image acquirer configured to acquire a moving image of a subject, a feature estimator configured to estimate a plurality of anatomical feature points of the subject by a predetermined posture recognition method for performing image recognition to recognize a posture of the subject from the moving image, a reference storage configured to store a reference length that is an actual length of a predetermined reference part, a motion analyzer configured to obtain, as a value for use in evaluation of motion of the subject, a value representing a motion state of the subject from a distance on the image between the plurality of anatomical feature points based on a ratio, to the reference length, of a distance on the image that is determined from the plurality of anatomical feature points estimated and corresponds to the reference part, and an outputter configured to output the value representing the motion state.

Herein, the "motion state evaluation system" may be a system including a combination of an information terminal that acquires the "moving image of the subject" and a server that obtains the "value representing the motion state" or may be a system in which the information terminal and the server cooperate together in the process of obtaining the "value representing the motion state". Alternatively, the "motion state evaluation system" may be a system only including an information terminal capable of performing both the process of acquiring the "moving image of the subject" and the process of obtaining the "value representing the motion state". The "system" may include one or more hardware elements of any type. The "predetermined posture recognition method" may be any algorithm by which a person is extracted from an image, and a posture of the person is recognized. The "plurality of anatomical feature points" may be connection parts between elements constituting a body of the person extracted from the image, ends of the elements, or boundary points between the elements. The "predetermined posture recognition method" may be a method for estimating, from an appearance of the person in the image, positions of the "plurality of anatomical feature points" based on the nature of an anatomical structure such as a skeleton originally possessed by humans or based on statistics on a positional relation with the appearance. The "predetermined posture recognition method" may be a method for recognizing the posture of the person from each of a plurality of frames included in the moving image, or may be a method for estimating changes in position of the "plurality of anatomical feature points" based on changes in appearance between the frames. The "predetermined posture recognition method" may be a method for performing the above-described various processes based on machine learning such as deep learning where a large number of moving images having the subject have been learned. The "predetermined reference part" may be a part that is predetermined as a reference for use in a process of estimating an actual length of the person or an actual length of an anatomical element of the person in the moving image, and the actual length of the "predetermined reference part" may be pre-stored as the "reference length". The "length" may be a distance or dimension between two points in space. The "value representing the motion state" may be a value of the motion state of the subject that can be obtained from positions of the anatomical feature points, distances of lines connecting the anatomical feature points, or an angle formed by the lines, or may be a value of another motion state that can be obtained from the value of the motion state or a time value. The "motion state" may be a posture in movement of the subject, such as a running form, a walking form, or an exercise form in any sport. The "value representing the motion state" may be a value of each of various parameters representing a state of the exercise form, such as a cadence, a body posture angle, a shoulder joint range of motion angle, or a hip joint range of motion angle obtained from a running speed, a step length, a vertical motion width, and a vertical motion cycle while the subject is running.

This embodiment makes it possible to accurately perform image-analysis on the moving image to analyze the motion state of the subject in response to only a simple operation made by the user to provide a useful evaluation.

The feature estimator may estimate a plurality of joint positions of the subject as the plurality of anatomical feature points, and the motion analyzer may obtain the value representing the motion state of the subject based on a ratio, to the reference length, of a distance between predetermined joints estimated on the image. The "joint positions" may be connection parts between elements constituting the body of the person extracted from the image, or may be positions estimated based on the nature of an anatomical structure such as a skeleton originally possessed by humans or based on statistics on a positional relation with the appearance. This embodiment makes it possible to estimate the "predetermined reference part" from the joint positions of the subject and obtain, based on a relation between the distance on the image of the "reference part" and the "reference length", various actual speeds, lengths, angles, and time values of the subject to accurately estimate the values of various parameters representing the motion state only through image-analysis.

The reference storage stores a height of the subject as the reference length, and the motion analyzer obtains, as the value for use in evaluation of motion of the subject, the value representing the motion state of the subject from a feature point distance on the image of the plurality of anatomical feature points based on a ratio, to the height, of a distance on the image that is determined from the plurality of anatomical feature points and corresponds to the height of the subject. Many users know their exact heights, so the entire body may be set as the "reference part", and the "height" that is a length of the entire body may be set as the "reference length", making it possible to easily use an accurate reference length. This makes it possible to easily obtain a more accurate value as the value representing the motion state.

The motion state evaluation system may further include an evaluation processor configured to evaluate the motion of the subject based on the value representing the motion state. The value representing the motion state may include a value based on a width of predetermined motion of the subject during exercise. The reference storage may further store a regression equation and a standard deviation as a result of regression analysis between a value based on the width of the predetermined motion during exercise that is predetermined through analysis of moving images of a plurality of other subjects and a value based on a physical condition of the subject, the regression equation having the value based on the physical condition as an explanatory variable and the value based on the width of the predetermined motion as an objective variable, the evaluation processor may calculate a tentative value of the value based on the width of the predetermined motion by substituting the value based on the physical condition of the subject into the regression equation, and evaluate the motion of the subject based on whether a difference between the value based on the width of the predetermined motion analyzed from the moving image of the subject and the tentative value falls within the standard deviation, and the outputter may output a result of the evaluation. The "value based on the width of the predetermined motion" may be a length, an angle, a time interval when a body part moves during a predetermined exercise, or another value obtained from these values. The "value based on the physical condition of the subject" may be a value having a correlation with particularly a value used as the objective variable in the regression equation out of values representing the physical condition of the subject under examination, a physical exercise level, physical exercise feature, and physical exercise attribute of the subject, and the like. The "value based on the physical condition" may be a value that results from analyzing the moving image of the subject, or may be any value included in the "value based on the width of the predetermined motion". The "regression equation" may be a single regression equation having one value as an explanatory variable or a multiple regression equation having a plurality of values as explanatory variables. For example, in order to evaluate the step length and cadence, a value such as a height, weight, age, gender, exercise speed, or level of a marathon time as the "value based on the physical condition of the subject" for a plurality of subjects may be used as an explanatory variable, and a regression equation including the step length or cadence at the speed as an objective variable and a standard deviation may be calculated in advance and stored as a regression analysis result. Herein, the "tentative value" may be a statistical standard value, median value, average value, or ideal value. Based on the regression analysis result, a tentative step length or cadence is calculated by substituting a value based on a physical condition of another subject into the regression equation, and a determination is made whether a difference between the tentative value and a step length or cadence estimated from the moving image falls within the standard deviation. As described above, it is possible to quantitatively and objectively evaluate the motion of the subject such as a running form from a relation between the predetermined parameters related to the motion state or physical condition of the subject and the other parameters.

The motion state evaluation system may further include an information storage configured to store advice information on the motion during exercise with the advice information and the evaluation result of the motion associated with each other. The evaluation processor may retrieve the advice information associated with the result of the evaluation of the motion of the subject from the information storage, and the outputter may output the advice information thus retrieved. The "advice information" may be a text, image, or voice representing a suggestion or explanation for the evaluation of the motion of the subject, a suggestion for improvement, an injury risk, or reference information, and the suggestion for improvement may be a suggestion for recommended training contents, exercise equipment, and shoes for exercise.

Another embodiment of the present invention is a motion state evaluation device. This device includes an image acquirer configured to acquire a moving image of a subject, a transmitter configured to transmit the moving image to a predetermined server over a network, a receiver configured to receive a value representing a motion state of the subject, the value being obtained, based on a ratio, to a reference length that is a prestored actual length of a predetermined reference part, of a distance on the image that is determined from a plurality of anatomical feature points of the subject estimated by a predetermined posture recognition method for performing image recognition to recognize a posture of the subject from the moving image in the server and corresponds to the reference part, from a distance on the image between the plurality of anatomical feature points, and an outputter configured to display the value representing the motion state on a screen.

This embodiment also makes it possible to accurately perform image-analysis on the moving image to analyze the motion state of the subject in response to only a simple operation made by the user to provide a useful evaluation.

Yet another embodiment of the present invention is also a motion state evaluation device. This device includes an image acquirer configured to acquire a moving image of a subject, a feature estimator configured to estimate a plurality of anatomical feature points of the subject by a predetermined posture recognition method for performing image recognition to recognize a posture of the subject from the moving image, a reference storage configured to store a reference length that is an actual length of a predetermined reference part, a motion analyzer configured to obtain, as a value for use in evaluation of motion of the subject, a value representing a motion state of the subject from a distance on the image between the plurality of anatomical feature points based on a ratio, to the reference length, of a distance on the image that is determined from the plurality of anatomical feature points estimated and corresponds to the reference part, and an outputter configured to display the value representing the motion state on a screen.

This embodiment also makes it possible to accurately perform image-analysis on the moving image to analyze the motion state of the subject in response to only a simple operation made by the user to provide a useful evaluation.

Yet another embodiment of the present invention is a motion state evaluation server. This motion state evaluation server includes a receiver configured to receive a moving image of a subject from a predetermined information terminal over a network, a feature estimator configured to estimate a plurality of anatomical feature points of the subject by a predetermined posture recognition method for performing image recognition to recognize a posture of the subject from the moving image, a reference storage configured to store a reference length that is an actual length of a predetermined reference part, a motion analyzer configured to obtain, as a value for use in evaluation of motion of the subject, a value representing a motion state of the subject from a distance on the image between the plurality of anatomical feature points based on a ratio, to the reference length, of a distance on the image that is determined from the plurality of anatomical feature points estimated and corresponds to the reference part, and an outputter configured to output the value representing the motion state.

This embodiment also makes it possible to accurately perform image-analysis on the moving image to analyze the motion state of the subject in response to only a simple operation made by the user to provide a useful evaluation.

Yet another embodiment of the present invention is a motion state evaluation method. This method includes acquiring a moving image of a subject, estimating a plurality of anatomical feature points of the subject by a predetermined posture recognition method for performing image recognition to recognize a posture of the subject from the moving image, obtaining, as a value for use in evaluation of motion of the subject, a value representing a motion state of the subject from a distance on the image between the plurality of anatomical feature points based on a ratio, to a reference length that is a prestored actual length of a predetermined reference part, of a distance on the image that is determined from the plurality of anatomical feature points estimated and corresponds to the reference part, and outputting the value representing the motion state.

This embodiment also makes it possible to accurately perform image-analysis on the moving image to analyze the motion state of the subject in response to only a simple operation made by the user to provide a useful evaluation.

Note that any combination of the above components, or an entity that results from replacing components or expressions of the present invention with each other among a method, a device, a program, a transitory or non-transitory storage medium storing the program, a system, and the like is also valid as an embodiment of the present invention.

BRIEF DESCRIPTION OF THE DRAWINGS

Embodiments will now be described by way of examples only, with reference to the accompanying drawings which are meant to be exemplary, not limiting and wherein like elements are numbered alike in several Figures in which:

FIG. 9 is a diagram schematically showing a training selection table defined as selection criteria for recommended training contents displayed in a recommended exercise information field shown in FIG. 8.

FIG. 10 is a diagram schematically showing a shoes selection table defined as selection criteria for recommended shoes displayed in a recommended gear information field shown in FIG. 8.

DETAILED DESCRIPTION OF THE INVENTION

First Embodiment

Figure 1:
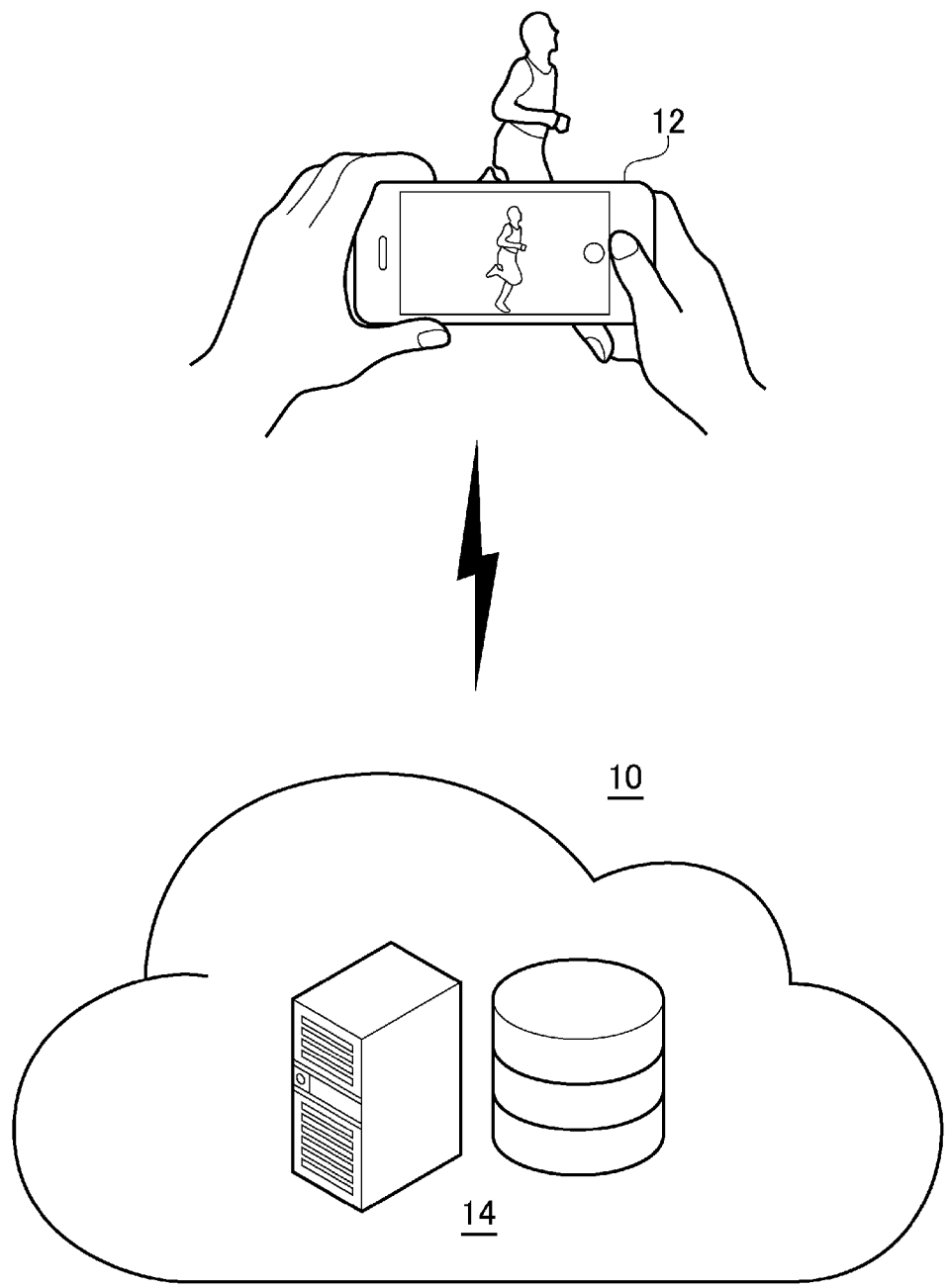
FIG. 1 is a diagram schematically showing a structure of a motion state evaluation system.

FIG. 1 schematically shows a structure of a motion state evaluation system 10. The motion state evaluation system 10 includes an information terminal 12 and an evaluation server 14, and the information terminal 12 and the evaluation server 14 cooperate together to make various functions implemented in the motion state evaluation system 10 work. According to the present embodiment, the information terminal 12 is responsible for acquiring a moving image of a subject and displaying a result of evaluation of motion on a screen, and the evaluation server 14 is responsible for analyzing the moving image and conducting the evaluation. The moving image of the subject acquired by the information terminal 12 is transferred to the evaluation server 14 over a communication means such as radio communication, and the evaluation server 14 analyzes the moving image and conducts the evaluation. The evaluation result is transferred to the information terminal 12 and displayed on the screen of the information terminal 12. The information terminal 12 is a mobile phone terminal such as a smartphone with a camera function or a tablet terminal with a camera function. According to a modification, a computer with a camera function or a computer to which a camera device is connected may be used as the information terminal 12. A program for analyzing the moving image of the subject and conducting the evaluation (motion state evaluation program) that runs on the information terminal 12 and the evaluation server 14 causes the information terminal 12 to function as a motion state evaluation device and causes the evaluation server 14 to function as a motion state evaluation server. According to the other embodiments including the following second embodiment (to be described later), a specification where the information terminal 12 is responsible for some of the process of analyzing the moving image and conducting the evaluation so as to divide the process between the information terminal 12 and the evaluation server 14 may be employed, or alternatively, a specification where the information terminal 12 is responsible for all the process of analyzing the moving image and conducting the and evaluation may be employed. Hereinafter, a description will be given of a configuration where the evaluation server 14 is responsible for all the process of analyzing the moving image and conducting the evaluation according to the present embodiment.

Figure 2:
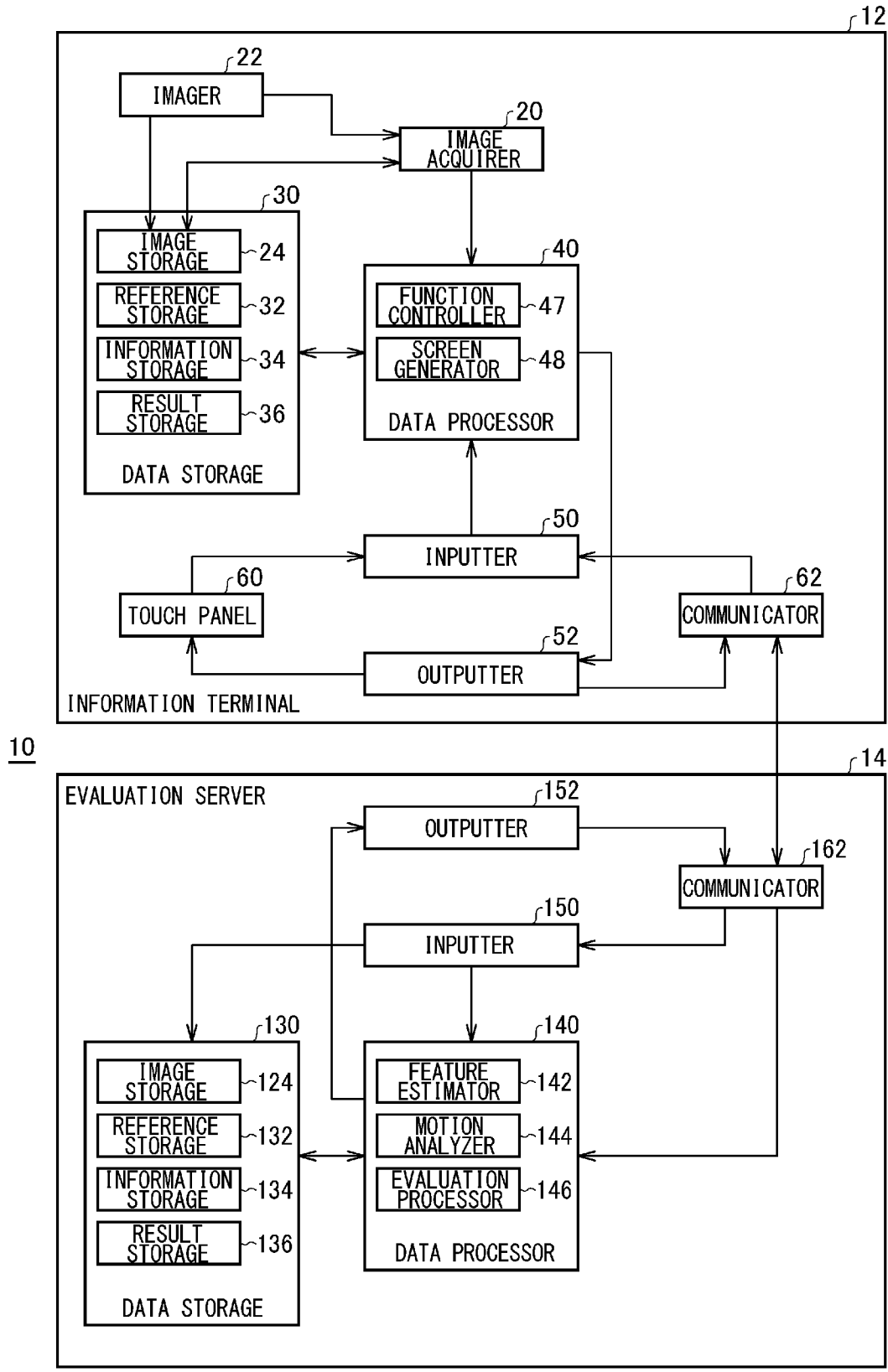
FIG. 2 is a functional block diagram showing basic structures of an information terminal and an evaluation server.

FIG. 2 is a functional block diagram showing basic structures of the information terminal 12 and the evaluation server 14. The information terminal 12 includes an image acquirer 20, an imager 22, a data storage 30, a data processor 40, an inputter 50, an outputter 52, a touch panel 60, and a communicator 62. The data storage 30 includes an image storage 24, a reference storage 32, an information storage 34, and a result storage 36. The data processor 40 includes a function controller 47 and a screen generator 48. The evaluation server 14 includes a data storage 130, a data processor 140, an inputter 150, an outputter 152, and a communicator 162. The data storage 130 includes an image storage 124, a reference storage 132, an information storage 134, and a result storage 136. The data processor 140 includes a feature estimator 142, a motion analyzer 144, and an evaluation processor 146.

FIG. 2 shows functional components for making the motion state evaluation system 10 work, and the other components are omitted. In FIG. 2, each element described as a functional block that performs various processes may be implemented with hardware such as a camera, a CPU, a GPU, a main memory, or a different type of large scale integrated circuit (LSI). Further, in terms of software, each element is implemented with a program and the like that are loaded into a RAM and then executed by the CPU. Therefore, it is understood by those skilled in the art that these functional blocks may be implemented in various forms such as hardware only, software only, and a combination of hardware and software, and therefore how to implement the functional blocks is not limited to any one of the above.

The image acquirer 20 acquires the moving image of the subject. The image acquirer 20 acquires, from the imager 22, the moving image captured by the imager 22, or acquires the moving image from the image storage 24. The imager 22 is, for example, a camera built in the information terminal 12 or an external camera connected to the information terminal 12. The image storage 24 is, for example, a non-volatile memory built in the information terminal 12 or a recording medium loaded or connected to the information terminal 12. The image storage 24 stores a still image and moving image captured by the imager 22 and the like.

The reference storage 32 prestores a reference length that is an actual length of a predetermined reference part, the reference length serving as an analysis reference in the motion state evaluation program. According to the present embodiment, the reference storage 32 stores a height of the subject as the reference length. A user inputs and sets, before activating the motion state evaluation program, his/her height with the touch panel 60 of the information terminal 12. Information on the height input with the touch panel 60 is stored in the reference storage 32 via the inputter 50 and the function controller 47.

The information storage 34 stores the motion state evaluation program, and an ID (for example, an e-mail address) and password of the user used for access to the motion state evaluation system 10. The result storage 36 stores a result of analyzing the moving image and a result of the evaluation (to be described later).

The function controller 47 controls a process such as input and output of information in order to activate various functions constituting the motion state evaluation program. The function controller 47 logs in to the evaluation server 14 with the ID and password of the user stored in the information storage 34. The function controller 47 transfers, as an object to be analyzed by the evaluation server 14, the moving image acquired by the image acquirer 20 to the evaluation server 14 via the outputter 52 and the communicator 62. At this time, when the user of the information terminal 12 is the subject, the information on the height of the user stored in the reference storage 132 is transferred to the evaluation server 14 together with the moving image. When a person other than the user of the information terminal 12 is the subject, the function controller 47 transfers the information on the height of the subject input from the touch panel 60 to the evaluation server 14 together with the moving image. A screen display function of the motion state evaluation program causes the screen generator 48 to generate a screen to be displayed on the touch panel 60 and to display the screen thus generated on the touch panel 60 via the outputter 52.

The inputter 150 receives the moving image and information on the height transmitted from the information terminal 12 via the communicator 162, temporarily stores the moving image in the image storage 124, and temporarily stores the information on the height in the reference storage 132. The feature estimator 142 estimates a plurality of anatomical feature points of the subject by a predetermined posture recognition method for performing image-recognition to recognize a posture of the subject from the moving image. The reference storage 132 prestores the reference length that is the actual length of the predetermined reference part. According to the present embodiment, the reference storage 132 temporarily stores the height of the subject as the reference length. The motion analyzer 144 obtains, as a value for use in evaluation of the motion of the subject, a value representing the motion state of the subject from a distance on the image between the plurality of anatomical feature points based on a ratio, to the reference length (a length in the metric system), of a feature point distance on the image (a distance in pixel units) that is determined from the plurality of anatomical feature points thus estimated and corresponds to the reference part. The evaluation processor 146 calculates a tentative value of a running form parameter by substituting a value based on a predetermined physical condition into a predetermined regression equation, and evaluates the motion of the subject based on whether a difference between a running form parameter analyzed from the moving image of the subject and the tentative value falls within a standard deviation. Herein, the value based on the physical condition is a value having a correlation with particularly a value used as an objective variable in the regression equation out of values representing the physical condition of the subject under examination, a physical exercise level, physical exercise feature, and physical exercise attribute of the subject, and the like. As the value based on the physical condition, any one of various running form parameters obtained through analysis of the moving image of the subject may be used. Further, the tentative value may be a statistical standard value, average value, or median value.

Estimation of Anatomical Feature Point

Figure 3:
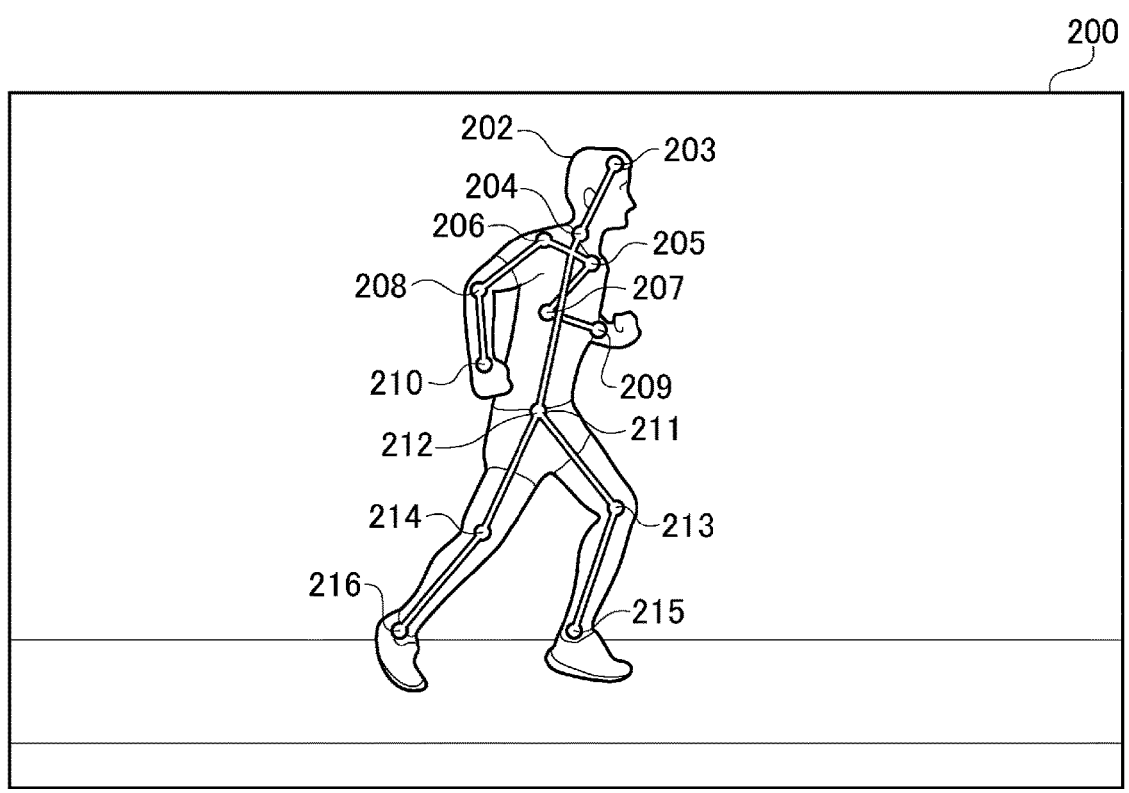
FIG. 3 is a diagram schematically showing a state where a plurality of anatomical feature points are estimated from a moving image of a subject who is running.

FIG. 3 schematically shows a state where the plurality of anatomical feature points are estimated from the moving image of the subject who is running. The feature estimator 142 estimates, as the plurality of anatomical feature points, a plurality of joint positions of the subject, for example, positions of limb joints (such as shoulders, elbows, wrists, hip joints, knees, and ankles). Further, the feature estimator 142 further estimates, as the plurality of anatomical feature points, positions of connection parts (such as a neck, a pelvis, and a thorax) other than the joints and positions of tip parts (such as the top of head and heels). In the example shown in FIG. 3, the feature estimator 142 estimates, from the moving image of the subject who is running, the positions of a top of head 203, a neck 204, a left shoulder 205, a right shoulder 206, a left elbow 207, a right elbow 208, a left wrist 209, a right wrist 210, a left hip joint 211, a right hip joint 212, a left knee 213, a right knee 214, a left ankle 215, and a right ankle 216. The feature estimator 142 may superimpose, on the moving image, a so-called stick picture in which the plurality of anatomical feature points are represented by circles and body parts connecting the anatomical feature points are represented by thick lines, as in the example shown in FIG. 3.

Any technology is applicable to the posture recognition method. For example, the anatomical feature points of the subject may be estimated from the moving image by markerless motion capture based on results of deep learning applied to a large number of moving images. As a markerless motion capture technology based on deep learning, "DeepPose: Human Pose Estimation via Deep Neural Networks" (Alexander Toshev, Christian Szegedy), "Convolutional Pose Machines" (Ship-En Wei, Varun Ramakrishna, Takeo Kanade, Yaser Sheikh), and "Realtime Multi-Person 2D Pose Estimation using Part Affinity Fields" (Zhe Cao, Tomas Simon, Shih-En Wei, Yaser Sheikh) are known, for example. As a markerless motion capture technology without using deep learning, "Articulated Human Pose Estimation with Flexible Mixtures of Parts" (Yi Yang and Deva Ramanan) is known, for example. According to another embodiment, a motion capture technology in which a marker or sensor is attached to each body part of the subject, and the anatomical feature points of the subject are estimated through recognition of the positions of the markers or sensors may be used. Since such capture technologies are publicly known, no detailed description of the technologies will be given. As described above, the use of such a markerless motion capture technology makes it possible to easily estimate the anatomical feature points of a human with a widely available device such as a camera built in a smartphone, without using equipment dedicated to motion capture.

The motion analyzer 144 obtains, for example, a distance on the image corresponding to the height of the subject based on a distance between predetermined joints estimated on the image. Specifically, in order to estimate a length from the head to the feet, distances on the image between body parts such as the top of head and the neck, the neck and the shoulders, the shoulders and the hip joint, the hip joint and the knees, the knees and the ankles, and the ankles and the heels are measured and then added up, and the sum of the distances is used as a height H on the image from the top of head to the heels. Note that when the feature estimator 142 fails to estimate the positions of the heels, a correction value resulting from multiplying the sum of the distances on the image from the top of head to the ankles by a predetermined correction factor (for example, 1.05) may be used as the height H on the image from the top of head to the heels. Alternatively, when the feature estimator 142 fails to estimate the position of the top of head, a correction value resulting from multiplying the sum of the distances on the image from the neck to the heels by a predetermined correction factor (for example, 1.1) or a correction value resulting from multiplying the sum of the distances on the image from the neck to the ankles by a predetermined correction factor (for example, 1.15) may be used as the height H on the image from the top of head to the heels.

Analysis of Running Form Parameter

The motion analyzer 144 obtains a ratio of the height H on the image thus obtained to the height of the subject serving as the reference length prestored in the reference storage 132, and takes the ratio as a conversion factor S with which a distance on the image is converted into a distance in the metric system. The motion analyzer 144 obtains, based on the conversion factor S, a value representing the motion state of the subject. The value representing the motion state is, for example, a parameter based on a width of a predetermined motion of the subject during exercise. According to the present embodiment, running form parameters (a speed, a step length, a vertical motion width as well as a cadence, a body posture angle, a shoulder joint range of motion, and a hip joint range of motion) that constitute the running form are obtained as values representing the motion state. That is, the motion analyzer 144 analyzes the moving image to obtain values of the various running form parameters. When a value thus obtained is a length value, the value is multiplied by the conversion factor S to convert into a value in the metric system. The values of the various running form parameters obtained through analysis of the moving image are hereinafter referred to as analysis values P. As described above, the use of the conversion factor S makes it possible to easily calculate the various running form parameters in the metric system by simple calculation without a complicated calibration work.

The motion analyzer 144 analyzes the running form parameters from a moving image that is obtained by capturing mainly a side of the subject who is running from a fixed capture position and in a fixed capture direction. For example, for a moving image that is obtained by capturing a right side of the subject, analysis is first made on anatomical feature points of the right half of the body, and for a moving image that is obtained by capturing a left side of the subject, analysis is first made on anatomical feature points of the left half of the body. The motion analyzer 144 determines that a timing at which a vertical position of the top of head of the subject becomes the minimum value in a vertical motion cycle of the subject is a ground contact timing. The motion analyzer 144 sets a ground contact timing determined for the first time after the start of recognizing the anatomical feature points as the first step, a ground contact timing at which the other foot comes into contact with the ground as the second step, and the next contact timing at which the same foot as the foot of the first step comes into contact with the ground as the third step, and the first to third steps are defined as one running cycle.

Herein, the "speed" as one of the running form parameters is a speed of travel by a distance between two points in the moving image (for example, a difference between positions where the head has moved in the horizontal direction), and may be an average speed value in one running cycle. The "step length" may be a distance equivalent to one step in the moving image, or may be a value resulting from dividing a distance from the first step to the third step (one running cycle) (for example, a difference between positions of grounding feet in the horizontal direction) by 2. The "cadence" may be the number of times of ground contact per minute, or may be a reciprocal of a time equivalent to one step (a time interval from one ground contact to the next ground contact). The "vertical motion width" may be a difference between the maximum value and the minimum value of the vertical position of the top of head in one running cycle. The "body posture angle" may be an average of angles formed by a straight line connecting the hip joint and the neck and a vertical line in one running cycle. The "shoulder joint range of motion" may be a difference between the maximum value and the minimum value of an angle formed by a straight line connecting the shoulder and elbow and the vertical line in one running cycle. The "hip joint range of motion" may be a difference between the maximum value and the minimum value of an angle formed by a straight line connecting the hip joint and the knee and the vertical line in one running cycle.

The motion analyzer 144 may further obtain, as running form parameters, a landing position of a foot (for example, a relative landing position to the vertical line passing through any one of the reference parts including the top of head, hip joint, and the knees) and a degree of waist depression (for example, the vertical position of the hip joint) when a side of the subject is captured. The motion analyzer 144 may further obtain, as running form parameters, a head tilt angle, a shoulder levelness, an upper body twist, an upper body shake, a pelvis levelness, an arm swing, a knee orientation, a foot orientation, a thigh twist in a swing phase, a swinging leg orientation, and a foot landing position when a front side of the subject is captured. The motion analyzer 144 may further obtain, as running form parameters, a grounding pattern (grounding order of a forefoot, a midfoot, a rearfoot), pronation (overpronation/oversupination), a lower leg varus, an orientation of a tip of kicking foot, and a lower leg raising when a back side of the subject is captured. Different types of running form parameters to be analyzed and evaluated by the motion analyzer 144 and the evaluation processor 146 are set depends on whether the moving image of the subject is captured from the side, the front, or the back of the subject. As described above, such various running form parameters are obtained from the moving image through image-analysis, thereby allowing the running form to be quantitatively analyzed.

Evaluation of Running Form Parameter

The evaluation processor 146 calculates a tentative value E of each of the various running form parameters by substituting a value based on the physical condition of the subject into a predetermined regression equation, and evaluates the motion of the subject based on whether a difference between the analysis value P that results from analyzing the moving image of the subject and the tentative value E falls within the standard deviation. The analysis result and the evaluation result are associated with the ID of the user and stored in the result storage 136, and then transmitted to the information terminal 12 and stored in the result storage 36. For example, in a case of a specification where the exercise speed, height, or the like of the subject under examination is used as a value V based on the physical condition of the subject, the reference storage 132 stores a regression equation (E=aV+b) having the exercise speed, height, or the like as an explanatory variable and the tentative value E of each of the running form parameters as an objective variable, and the standard deviation SD for each of the running form parameters. In this case, the motion analyzer 144 may calculate an actual exercise speed by analyzing the exercise speed of the subject on the image from the moving image of the subject and multiplying the speed by the conversion factor S.

Figure 4A:
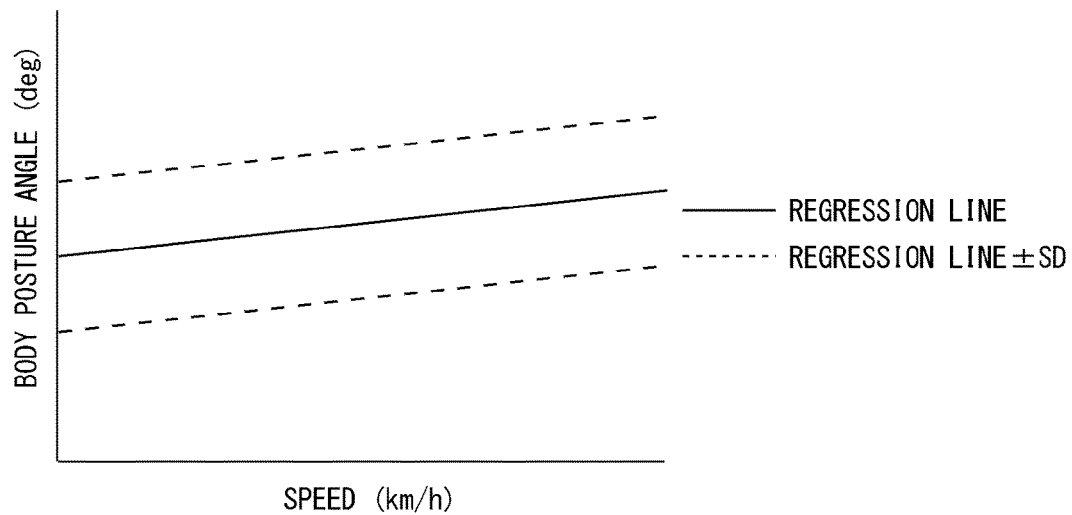
FIGS. 4A and 4B are diagrams showing examples of regression lines and standard deviations obtained from distributions of various running form parameters with respect to values based on a physical condition.
Figure 4B:
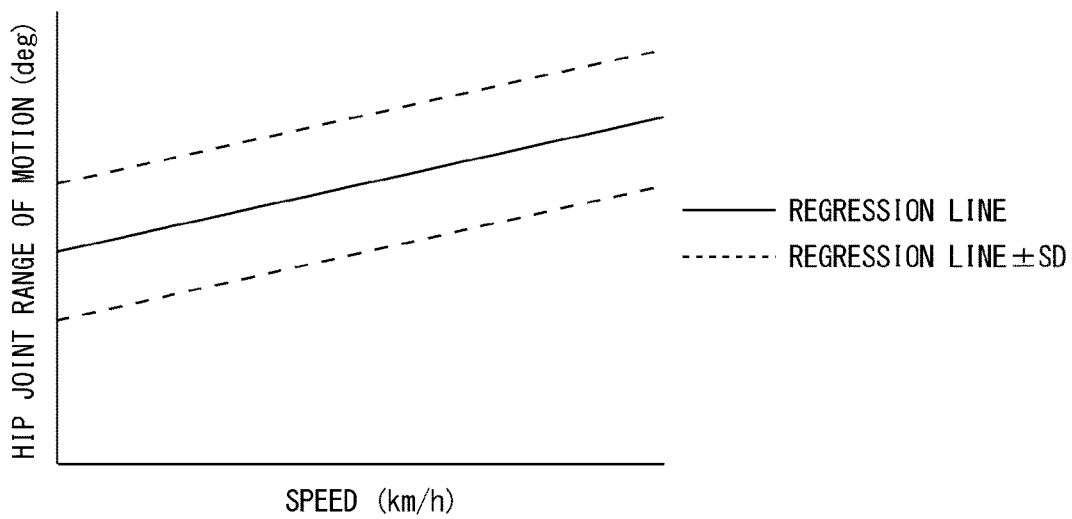

FIGS. 4A and 4B are diagrams showing examples of regression lines and standard deviations obtained from distributions of the various running form parameters with respect to the value based on the physical condition. As shown in FIGS. 4A and 4B, the regression lines and standard deviations are determined from distributions of sample data obtained in advance from a large number of subjects. FIG. 4A shows a regression line and standard deviation of the body posture angle with respect to the value based on the physical condition, and FIG. 4B shows a regression line and standard deviation of a hip joint range of motion angle with respect to the value based on the physical condition. The value based on the physical condition is, for example, the exercise speed, the height, or the like. In the examples shown in FIGS. 4A and 4B, the regression lines and standard deviations are obtained from distributions of the body posture angle and hip joint range of motion angle with respect to the exercise speed. As shown in FIGS. 4A and 4B, the regression equation and standard deviation are calculated from each distribution and prestored in the reference storage 132.

The evaluation processor 146 evaluates a case where the analysis value P is greater than the tentative value E+the standard deviation SD to be "greater than standard", evaluates a case where the analysis value P is less than the tentative value E−the standard deviation SD to be "less than standard", and evaluates a case where the analysis value P falls within a range of the tentative value E±standard deviation SD to be "standard". The evaluation processor 146 transmits the analysis value P, the tentative value E, the standard deviation SD, and information on the evaluation result of each of the various running form parameters to the information terminal 12 via the outputter 152 and the communicator 162. Note that various specifications can be considered as to which information the evaluation processor 146 transmits to the information terminal 12 as a result of analysis or evaluation. For example, either a specification where the evaluation processor 146 generates a display screen for the evaluation result and transmits data representing the screen to the information terminal 12 or a specification where the analysis value P, the regression equation, and the standard deviation SD are transmitted to the information terminal 12, and then the information terminal 12 conducts the evaluation based on the tentative value E and the standard deviation SD may be employed. Alternatively, a specification where, with the regression equation and the standard deviation SD prestored in the information terminal 12, only the analysis value P is transmitted to the information terminal 12, and then the information terminal 12 conducts the evaluation may be employed. Note that, as a modification, a specification where the analysis value P of the subject is evaluated by an evaluation method without using a regression analysis. For example, as statistics on the various running form parameters, an average value of each parameter classified by attribute such as gender, age, height, weight, or the like is stored, and the evaluation may be conducted by comparing the average values.

Figure 5:
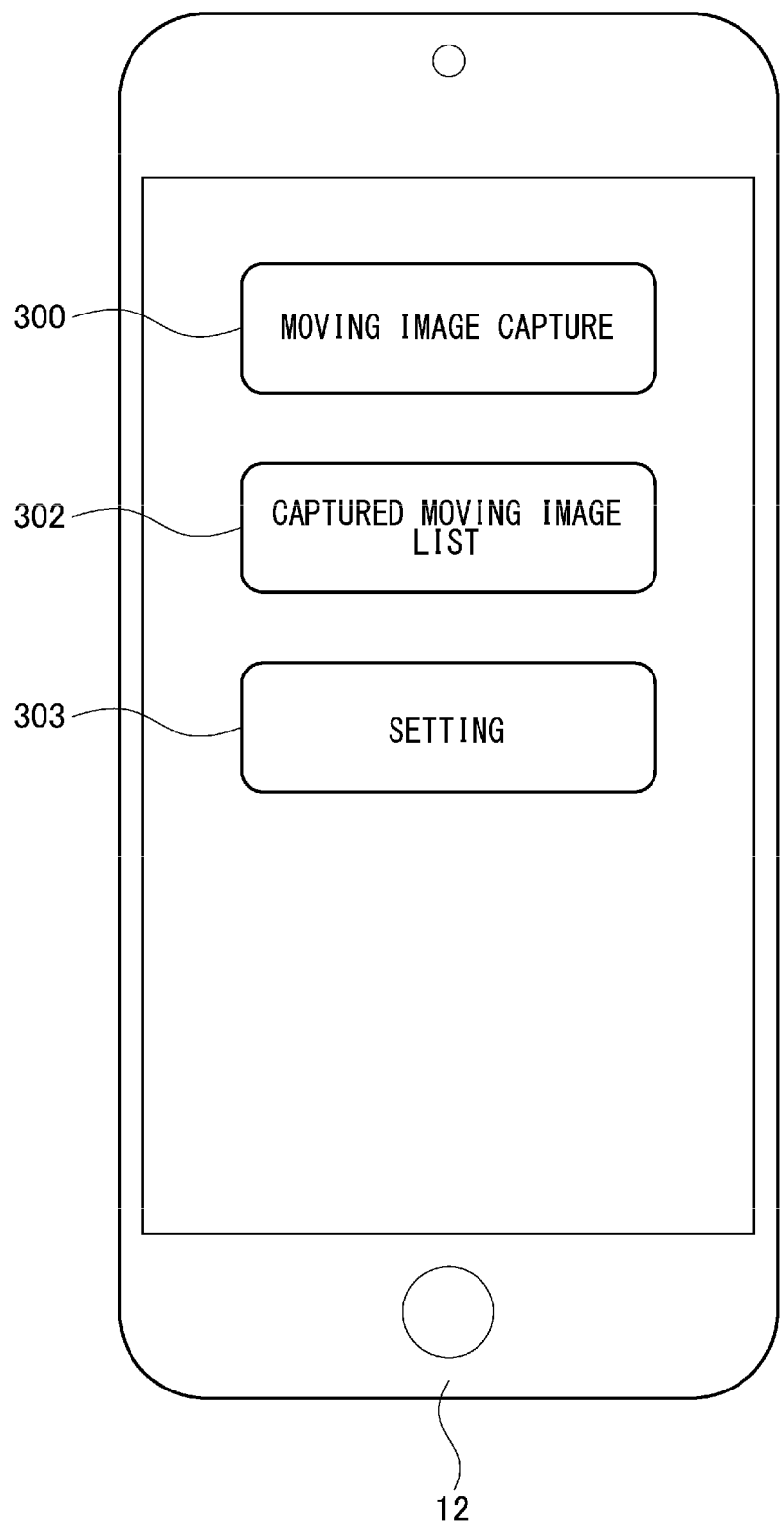
FIG. 5 is a diagram schematically showing an example of a menu screen of a motion state evaluation program.

FIG. 5 schematically shows an example of a menu screen of the motion state evaluation program. On the screen of the touch panel 60 of the information terminal 12, a moving image capture button 300, a captured moving image list button 302, and a setting button 303 are displayed. When the user presses (taps on) the moving image capture button 300, the imager 22 starts to capture a moving image, and the image acquirer 20 acquires the moving image thus captured. When the user presses the captured moving image list button 302, captured moving images stored in the image storage 24 are displayed in list form, and the image acquirer 20 acquires a moving image selected from the list. When the user presses the setting button 303, a transition is made to a screen for setting an ID, password, height, and the like of the user where the user can register or change these pieces of information.

Figure 6:
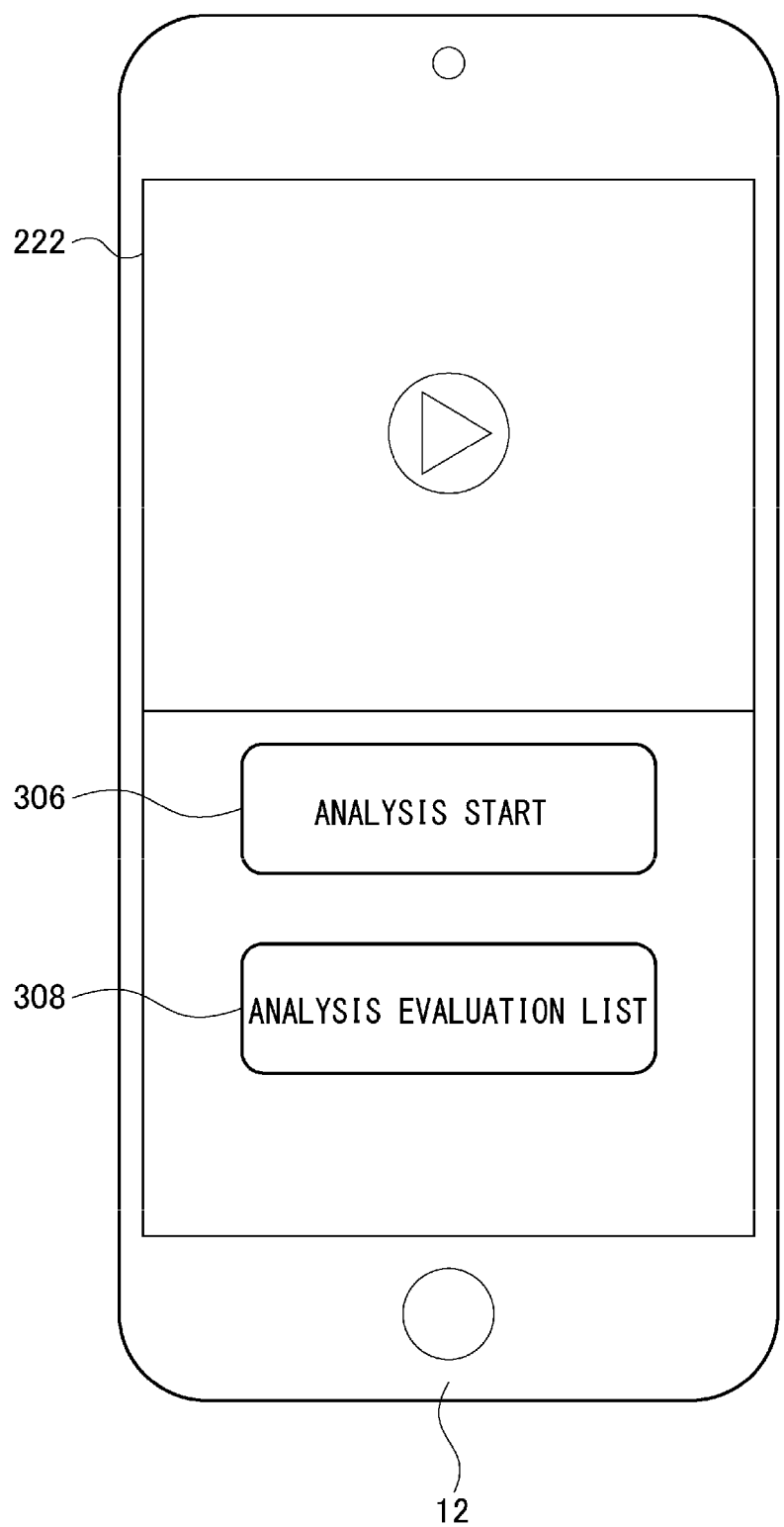
FIG. 6 is a diagram schematically showing an example of a screen for starting analysis and evaluation of the moving image.

FIG. 6 schematically shows an example of a screen for starting analysis of a moving image and conducting evaluation. On the screen of the touch panel 60 of the information terminal 12, a moving image reproducing screen 222, an analysis start button 306, and an analysis evaluation list button 308 are displayed. On the moving image reproducing screen 222, a captured moving image is reproduced and displayed. When the user presses the analysis start button 306, the captured moving image is transferred to the evaluation server 14, and analysis and evaluation processes are started. When the user presses the analysis evaluation list button 308, records of analysis and evaluations are displayed in list form, thereby allowing a past analysis and evaluation to be displayed.

Moving Image Reproducing Screen

Figure 7:
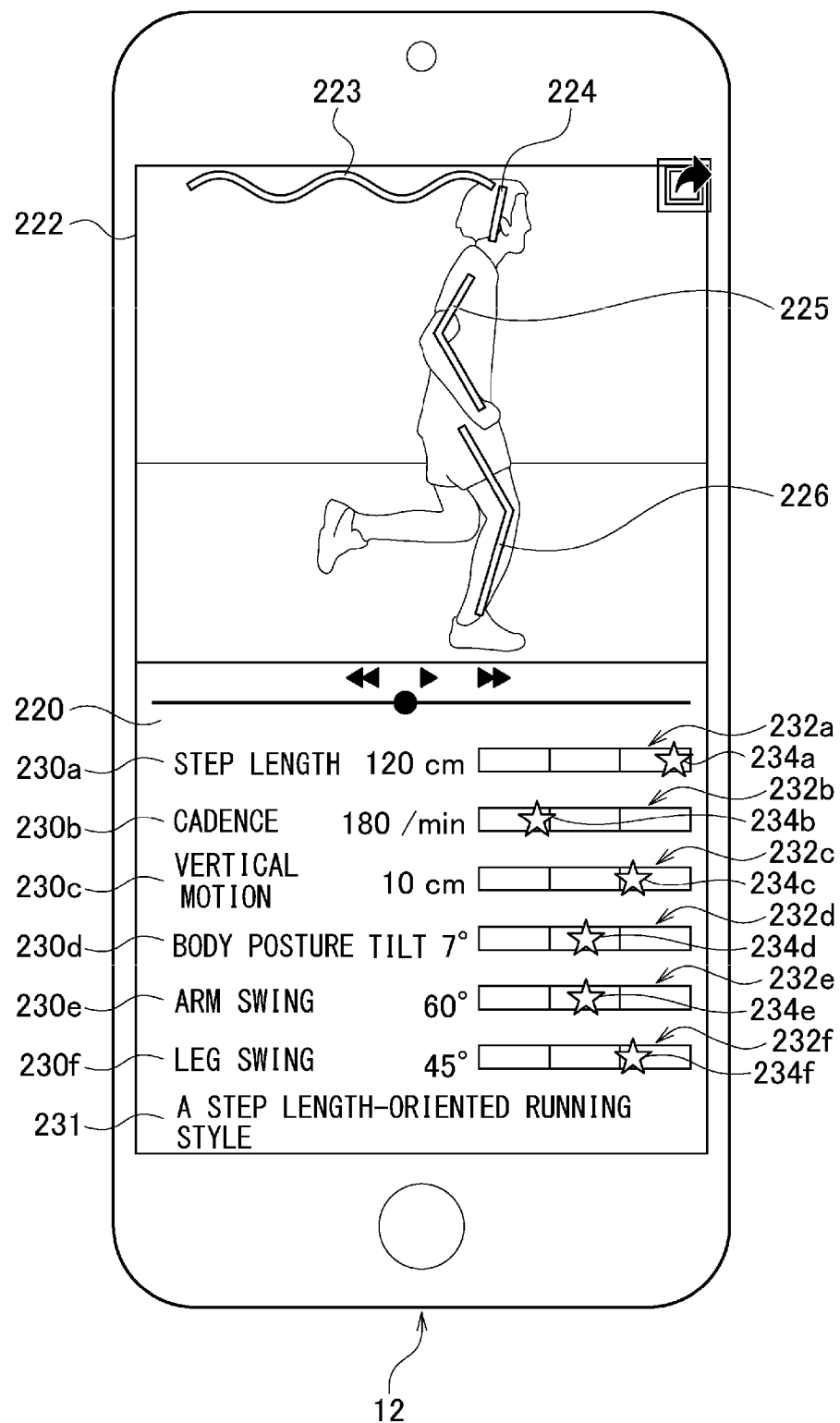
FIG. 7 is a diagram showing an example of a screen where the moving image and evaluation results are displayed.

FIG. 7 shows an example of a screen where the moving image and the evaluation result are displayed. The screen shown in FIG. 7 is generated by the screen generator 48. On the moving image reproducing screen 222 in the upper half of the screen, the captured moving image of the subject and the analysis result of the captured moving image are displayed. As the analysis result, for example, a line of a vertical motion path 223 representing a path of movement of the top of head in the moving image, a head highlighted line 224, an arm highlighted line 225, and a leg highlighted line 226 for highlighting positions and angles of the head, arms, and legs of the subject are dynamically superimposed and displayed on the image of the subject. At this time, as shown in FIG. 3, the plurality of anatomical feature points and lines of body parts connecting the feature points may be dynamically superimposed and displayed on the image of the subject as a stick picture. In order to make the motion of the subject and the analysis result easily recognizable, the moving image may be reproduced in slow motion. As described above, it is possible to visually grasp features of a form with ease.

Evaluation Screen

An evaluation screen 220 in the lower half of the screen includes a step length display field 230a, a cadence display field 230b, a vertical motion display field 230c, a body posture display field 230d, a shoulder joint range of motion display field 230e, and a hip joint range of motion display field 230f for displaying the analysis values and evaluation result of each of the various running form parameters in addition to an overall evaluation display field 231 for displaying the evaluation result regarding a tendency of an entire running form.

For example, "120 cm" is displayed as the analysis value P of the step length in the step length display field 230a, and a star 234a is displayed at a right end of a right evaluation gauge 232a. The evaluation gauge is divided into three areas: a left range, a center range, and a right range. The center range is a "standard" range of the tentative value E±1SD, the left range is a "less than standard" range of the tentative value E−3SD (three times the standard deviation) to E−1SD obtained from the regression equation, the right range is a "greater than standard" range of the tentative value E+1SD to E+3SD. The star 234a displayed at the right end of the evaluation gauge 232a indicates the "greater than standard" evaluation.

In the cadence display field 230b, "180 per minute" is displayed as the analysis value P of the cadence, and a star 234b is displayed in the left range of a right evaluation gauge 232b. The position of the star 234b indicates the "less than standard" evaluation. In the vertical motion display field 230c, "10 cm" is displayed as the analysis value P of the vertical motion, and a star 234c is displayed in the right range of a right evaluation gauge 232c. The position of the star 234c indicates the "greater than standard" evaluation. In the body posture display field 230d, "7°" is displayed as the analysis value P of the body posture angle, and a star 234d is displayed in the center range of a right evaluation gauge 232d. The position of the star 234d indicates the "standard" evaluation. In the shoulder joint range of motion display field 230e, "60°" is displayed as the analysis value P of the angle range of an arm swing width, and a star 234e is displayed in the center range of a right evaluation gauge 232e. The position of the star 234e indicates the "standard" evaluation. In the hip joint range of motion display field 230f, "45°" is displayed as the analysis value P of the angle range of a leg swing width, and a star 234f is displayed in the right range of a right evaluation gauge 232f. The position of the star 234f indicates the "greater than standard" evaluation.

When the step length is "greater than standard", and the cadence is "less than standard" or "standard" among the running form parameters, a "A STEP LENGTH-ORIENTED RUNNING STYLE" evaluation is displayed on the overall evaluation display field 231. On the other hand, when the step length is "less than standard" or "standard", and the cadence is "greater than standard", a "A STEP FREQUENCY-ORIENTED RUNNING STYLE" evaluation is displayed on the overall evaluation display field 231. As described above, the user can quantitatively and objectively grasp the features of his/her form by comparing the statistical standard value, median value, and average value.

Note that different colors may be applied to the left range, the center range, and the right range of the evaluation gauge 232 to facilitate visual distinction. For example, a gradation display in which a center of the left range is colored blue, a center of the center range is colored yellow, a center of the right range is colored red, and each of the color gradually changes from the left end to the right end of the evaluation gauge 232 may be applied. This makes it possible to visually grasp the features of the form with ease. The evaluation processor 146 may further evaluate an injury risk and running economy (running efficiency), and display the evaluation result on the screen as shown in FIG. 7.

Injury Risk Evaluation

The evaluation processor 146 may evaluate the injury risk based on the running form parameters. For example, a relation between each parameter and injury is predetermined by statistical analysis based on running form parameters of a large number of runners and information on the presence or absence of injury. That is, an injury function for calculating the injury risk is created through statistical analysis using the presence or absence of injury as an objective variable and the running form parameters as explanatory variables, and stored in the reference storage 132. The evaluation processor 146 substitutes the analysis value P of each of various running form parameters into the injury function to evaluate the presence or absence of the injury risk. This allows the user to quantitatively and easily recognize his/her injury risk only through image-analysis of the moving image, and therefore it can be expected to avoid injury.

Running Economy Evaluation

The evaluation processor 146 may evaluate the running economy based on the running form parameters. The running economy is an index indicating that the smaller the energy or oxygen intake required for running at a constant speed is, the higher the efficiency becomes. For example, a relation between the running form parameters of a large number of runners and the running economy of each runner is predetermined through statistical analysis. In other words, an economy function for calculating the running economy is created through statistical analysis using the running economy (a submaximal oxygen intake during running at a predetermined speed below the maximum) as an objective variable and the running form parameters as explanatory variables, and stored in the reference storage 132. The evaluation processor 146 substitutes the analysis value P of each of various running form parameters into the economy function to estimate the running economy, and evaluates the efficiency. Furthermore, the evaluation processor 146 may estimate a marathon time based on the running economy thus estimated. For example, a relation between running economy of a large number of runners and a marathon time of each runner is predetermined through statistical analysis. In other words, a marathon time function for calculating the marathon time is created through statistical analysis using the marathon time as an objective variable and the running economy (a submaximal oxygen intake during running at the predetermined speed below the maximum) as an explanatory variable, and stored in the reference storage 132. In this case, when the economy function is used as the explanatory variable of the marathon time function, a function for estimating the marathon time from the various running form parameters can be derived. The evaluation processor 146 can estimate the marathon time by substituting, into the marathon time function, a value of the running economy obtained by substituting the analysis value P of each of the various running form parameters into the economy function. As described above, the user can easily know his/her own efficiency and marathon estimation time only through image-analysis of the moving image, which can contribute to improvements in efficiency and time.

Form Comparison

On the moving image reproducing screen 222, not only the moving image of the subject but also a moving image of another person or a past moving image of the user may be reproduced and displayed in a manner as to make the moving image of another person or the past moving image of the user comparable to the moving image of the current subject. For example, a moving image of a model runner as a good example and information on his/her anatomical feature points are stored in the information storage 34 or the information storage 134, and instead of or in parallel to the moving image of the subject, the moving image of the model runner and its stick picture are reproduced and displayed. When past moving images of the user are stored as past records, the current and past moving images and their stick pictures may be reproduced in a comparable manner. Further, a moving image of another person or a past moving image of the subject may be superimposed on the moving image of the subject and displayed. In this case, any of the moving images to be superimposed may be made transparent. Further, the stick picture may be also superimposed and displayed, or only the stick picture may be superimposed and displayed instead of the moving image. Alternatively, instead of the moving image or the stick picture, an animation character may be superimposed and displayed as a moving image effect. As described above, the user can visually and easily compare the ideal form with his/her own form, which can contribute to an improvement in form. Further, it is possible for the user to visually and easily grasp a change in his/her own form.

Evaluation Score Comparison

The evaluation processor 146 may convert the evaluation into a numerical form by calculating an evaluation score based on a ratio, to the standard deviation SD, of the difference between the analysis value P and the tentative value E. The evaluation score may be calculated for each of the running form parameters, and the sum of the evaluation scores may be compared with an evaluation score of another person or a past evaluation score of the user and displayed on the evaluation screen 220. Further, the comparison with the evaluation score of another person or the past evaluation score of the user may be displayed in the form of a ranking table. This allows the user to quantitatively and easily check the change in his/her form.

As described above, the analysis result and the evaluation result are fed back to the user with a display of the results on the screen of the information terminal 12. As a feedback method other than such a screen display, a running form parameter having a low evaluation score calculated by the evaluation processor 146 can be fed back with a voice or vibration. For example, when the difference between the analysis value P and tentative value E of each parameter such as step length, vertical motion, cadence, and body posture angle is greater than the standard deviation SD, the user is notified by voice feedback or vibration feedback before or during running in an application program that records a running log. In those cases, for example, voice feedback "be conscious of making step length shorter" is output to a user who is evaluated as having a too long step length, and voice feedback "be conscious of suppressing vertical motion" is output to a user who is evaluated as having large vertical motion. For example, voice or vibration at optimal cadence time intervals in accordance with the current running speed can be given to a user who is evaluated as having too low or too high cadence to cause the user to be conscious of an ideal cadence. For example, a user who is evaluated as having a too large or too small body posture angle is recommended to purchase and wear a sensor that measures the body posture angle, and the user can be notified by voice or vibration generated when the body posture angle becomes too small or too large during running while wearing the sensor.

Advice Information

Figure 8:
FIG. 8 is a diagram showing an example of a screen where advice information is displayed.

FIG. 8 is a diagram showing an example of a screen where advice information is displayed. The information storage 134 stores the advice information on the motion during exercise with the advice information and the evaluation result of the motion associated with each other. The evaluation processor 146 retrieves the advice information associated with the result of the evaluation of the motion of the subject from the information storage 134. The advice information thus retrieved is transmitted to the information terminal 12 via the outputter 152 and the communicator 162. A screen as shown in FIG. 8 is generated by the screen generator 48. On the screen of the information terminal 12, an improvement information field 240, a recommended exercise information field 242 and a recommended gear information field 244 are displayed. In the improvement information field 240, a description of a point to be improved in the running form is displayed as advice information. In the recommended exercise information field 242, a description of recommended training contents is displayed as advice information. In the recommended gear information field 244, a description of recommended running shoes is displayed as advice information. As described above, the user can grasp not only the current status of the running form but also a point to be improved, an effective training method, and appropriate gear as advice on improvement in the form, and thus can promote the improvement.

FIG. 9 is a diagram schematically showing a training selection table defined as selection criteria for the recommended training contents displayed in the recommended exercise information field 242 shown in FIG. 8. A training selection table 250 is prestored in the reference storage 132. In the training selection table 250 shown in FIG. 9, four selection patterns are given as examples. A first pattern is selected when the step length is evaluated to be "smaller than standard", and "training No. 1" is displayed in the recommended exercise information field 242 shown in FIG. 8 as the recommended training. A second pattern is selected when the body posture angle is evaluated to be "greater than the standard", and "training No. 2" is displayed in the recommended exercise information field 242 shown in FIG. 8 as the recommended training. A third pattern is selected when the vertical motion is evaluated to be "greater than standard", and "training No. 3" is displayed in the recommended exercise information field 242 shown in FIG. 8 as the recommended training. A fourth pattern is selected when the arm swing width is evaluated to be "smaller than standard", and "training No. 4" is displayed in the recommended exercise information field 242 shown in FIG. 8 as the recommended training.

FIG. 10 is a diagram schematically showing a shoes selection table defined as recommended shoes selection criteria displayed in the recommended gear information field 244 shown in FIG. 8. A shoes selection table 260 is prestored in the reference storage 132. In the shoes selection table 260 shown in FIG. 10, twelve selection patterns are given as examples. In each of the selection patterns, a marathon time zone, normal running pace zone, and form type of the user who is the subject are associated with each other, thereby defining a runner level for each recommended type of shoes. For example, first and second patterns are associated with a marathon time of less than 2 hours and 30 minutes, third and fourth patterns are associated with a marathon time of 2 hours 30 minutes to 3 hours, fifth and sixth patterns are associated with a marathon time of 3 hours to 3 hours and 30 minutes, seventh and eighth patterns are associated with a marathon time of 3 hours 30 minutes to 4 hours, ninth and tenth patterns are associated with a marathon time of 4 hours to 4 hours and 30 minutes, and eleventh and twelfth patterns are associated with a marathon time of 4 hours and 30 minutes or more. Note that, when the marathon time is unknown, such as when the user has never run a marathon or has forgotten his/her marathon time, a normal pace is associated with each of the patterns so as to allow the user to select a marathon time in accordance with a normal running pace. For example, the first and second patterns are associated with less than 4 minutes per kilometer, the third and fourth patterns are associated with 4 to 4.5 minutes per kilometer, the fifth and sixth patterns are associated with 4.5 to 5 minutes per kilometer, the seventh and eighth patterns are associated with 5 to 5.5 minutes per kilometer, the ninth and tenth patterns are associated with 5.5 to 6 minutes per kilometer, and the eleventh and twelfth patterns are associated with 6 minutes or more per kilometer.

The first, third, fifth, and seventh patterns are associated with "step length type" when the running form is evaluated to be "step length type", and the second, fourth, sixth, and eighth patterns are associated with "cadence type" when the running form is evaluated to be "cadence type". Further, the ninth and eleventh patterns are associated with "overpronation" when the running form is evaluated to be "overpronation", and the tenth and twelfth patterns are associated with "underpronation" (oversupination, supination) when the running form is evaluated to be "underpronation".

Based on the above criteria, pattern candidates for recommended shoes are narrowed down to two in accordance with the marathon time or normal pace of the subject, one type of recommended shoes is further selected in accordance with the form and then displayed in the recommended gear information field 244 shown in FIG. 8.

Figure 11:
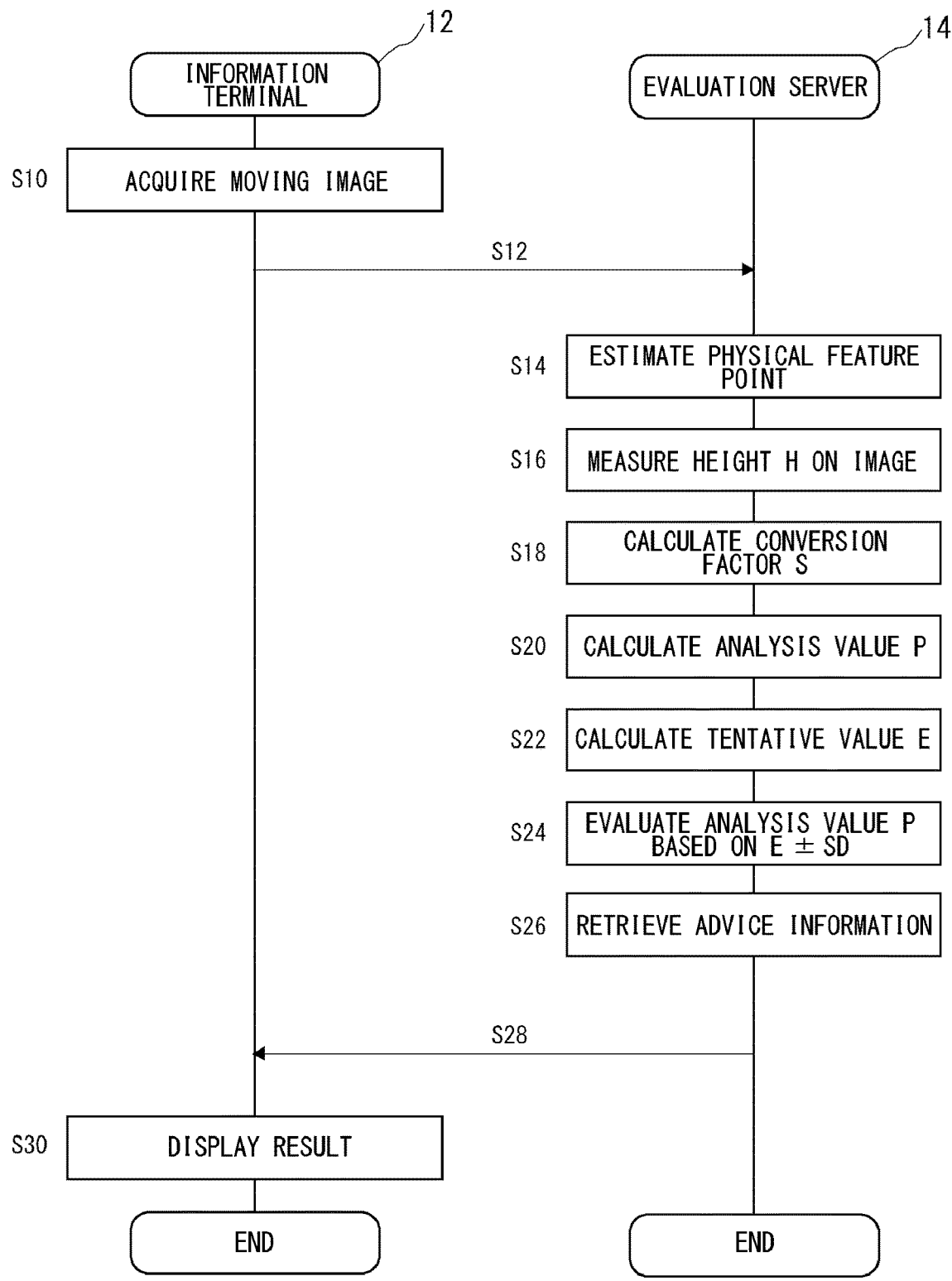
FIG. 11 is a flowchart showing a data flow between the information terminal and the evaluation server, and a process of analyzing the moving image and conducting evaluation.

FIG. 11 is a flowchart showing a data flow between the information terminal 12 and the evaluation server 14, and a process of analyzing the moving image and conducting evaluation. First, the image acquirer 20 acquires the moving image of the subject (S10), and the outputter 52 and the communicator 62 transfer the moving image to the evaluation server 14 (S12). The feature estimator 142 estimates a plurality of anatomical feature points from the moving image thus received (S14), the motion analyzer 144 measures the height H on the image (S16) and calculates the conversion factor S based on the ratio, to the prestored height of the subject, of the height H (S18). The motion analyzer 144 analyzes the values of the various running form parameters from the moving image and calculates the analysis value P by multiplying a length value by the conversion factor S (S20). The evaluation processor 146 calculates the tentative value E for each of the various running form parameters by substituting a value based on the physical condition as an explanatory variable into the regression equation for each parameter (S22) and conducts the evaluation based on whether the analysis value P for each parameter falls within the range of the tentative value E±the standard deviation SD (S24). The evaluation processor 146 retrieves the advice information in accordance with the evaluation result (S26), and the outputter 152 and the communicator 162 transmit the analysis result, evaluation result, and advice information to the information terminal 12

(S28), and the outputter 52 displays the result display screen generated by the screen generator 48 on the touch panel 60 (S30).

Note that, as a modification of the first embodiment, a specification where the evaluation processor is provided not only in the evaluation server 14 but also in the information terminal 12, and the reference storage 32 stores the advice information may be employed. In this case, the evaluation processor 146 in the evaluation server 14 may evaluate the various running form parameters, and based on the evaluation result, the evaluation processor in the information terminal 12 may retrieve the advice information associated with the evaluation result from the information storage 34 and display the advice information on the screen.

Second Embodiment

Figure 12:
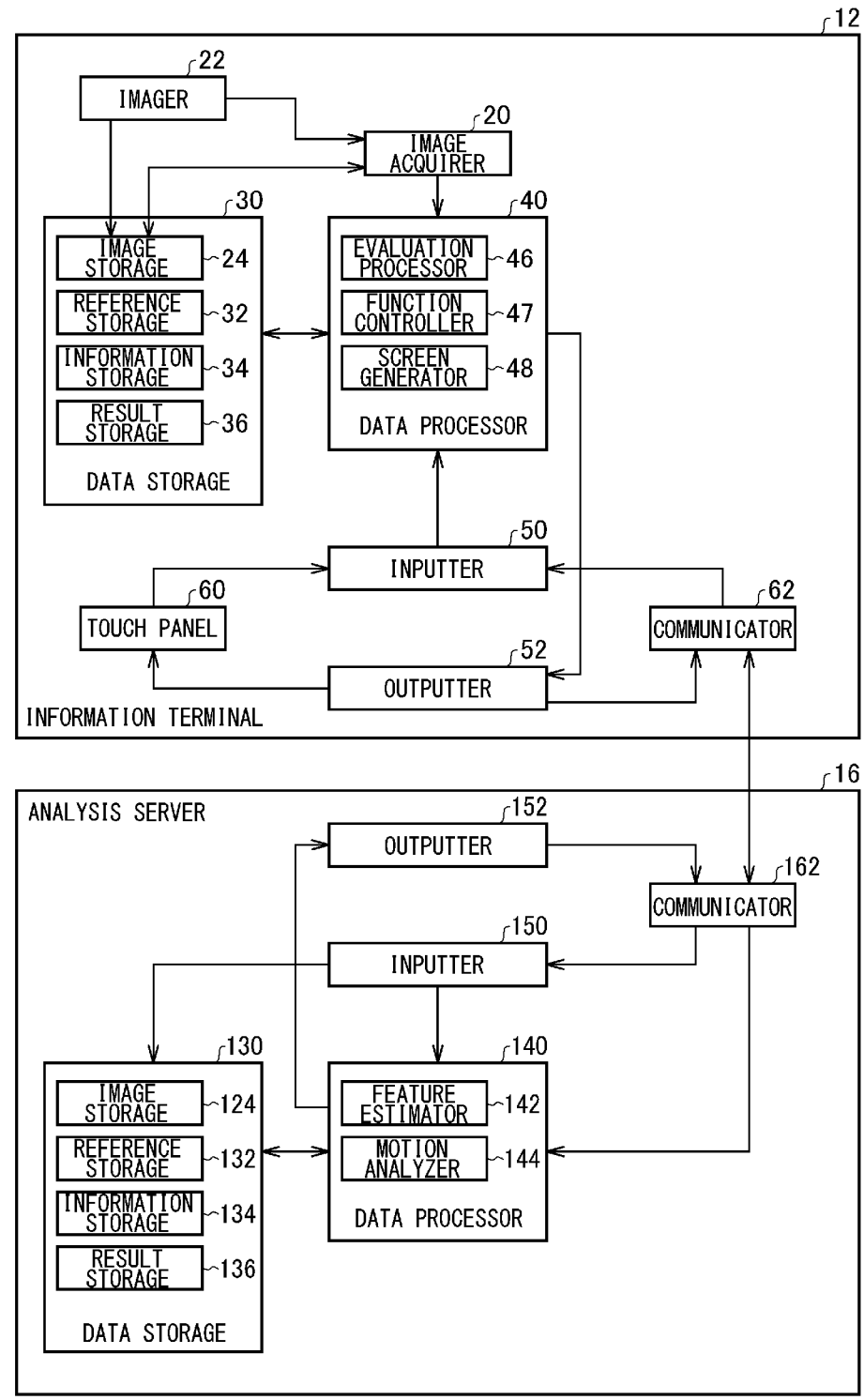
FIG. 12 is a functional block diagram showing basic structures of an information terminal and an analysis server according to a second embodiment.

FIG. 12 is a functional block diagram showing basic structures of the information terminal 12 and an analysis server 16 according to a second embodiment. A motion state evaluation system 10 according to the present embodiment is different from the motion state evaluation system 10 according to the first embodiment in that the motion state evaluation system 10 according to the present embodiment includes the information terminal 12 and the analysis server 16, and the "evaluation processor" is provided in the information terminal 12 rather than in a server (analysis server 16). Hereinafter, a description will be given mainly of differences from the first embodiment, and no description will be given of common points.

The analysis values P of the various running form parameters analyzed by the motion analyzer 144 are transmitted to the information terminal 12 by the outputter 152 and the communicator 162. The reference storage 32 of the information terminal 12 stores a regression equation (E=aV+b) having a value V based on the physical condition such as the exercise speed, height, or the like as an explanatory variable and a tentative value E of each of the running form parameters as an objective variable, and a standard deviation SD for each of the running form parameters. The evaluation processor 46 calculates the tentative value E of each of the various running form parameters by substituting the value based on the physical condition as an explanatory variable into the regression equation, and evaluates the motion of the subject based on whether a difference between the analysis value P transmitted from the analysis server 16 and the tentative value E falls within the standard deviation. The analysis result and the evaluation result are stored in the result storage 36.

The information storage 34 stores the advice information on the motion during exercise with the advice information and the evaluation result of the motion associated with each other. The data processor 40 includes the evaluation processor 46, the function controller 47, and the screen generator 48. The evaluation processor 46 retrieves the advice information associated with the result of the evaluation of the motion of the subject from the information storage 34. The advice information thus retrieved is displayed on the screen generated by the screen generator 48.

Figure 13:
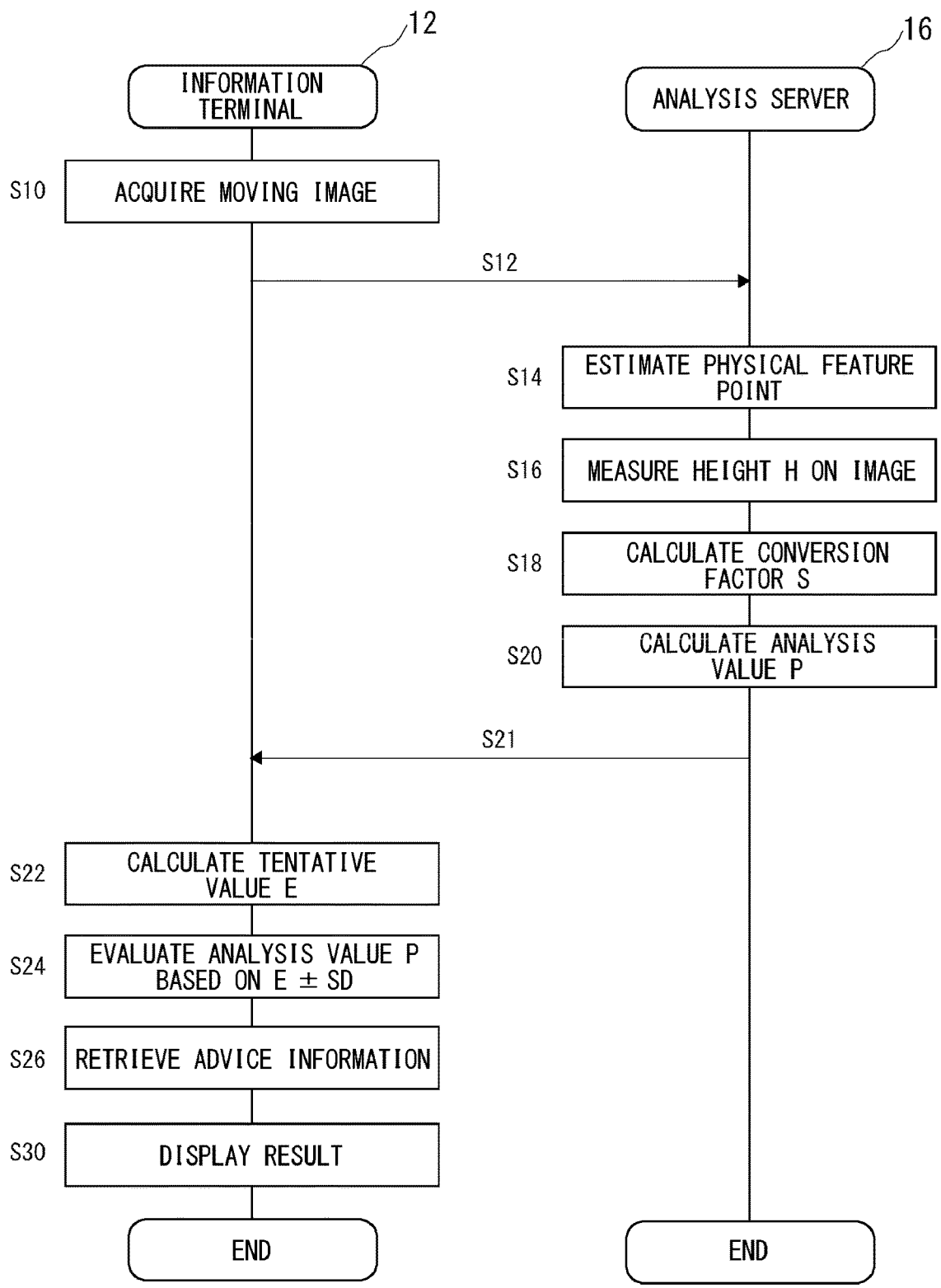
FIG. 13 is a flowchart showing a data flow between the information terminal and the analysis server, and a process of analyzing the moving image and conducting evaluation.

FIG. 13 is a flowchart showing a data flow between the information terminal 12 and the analysis server 16, and a process of analyzing the moving image and conducting evaluation. First, the image acquirer 20 acquires the moving image of the subject (S10), and the outputter 52 and the communicator 62 transfer the moving image to the evaluation server 14 (S12). The feature estimator 142 estimates a plurality of anatomical feature points from the moving image thus received (S14), the motion analyzer 144 measures the height H on the image (S16) and calculates the conversion factor S based on the ratio, to the prestored height of the subject, of the height H (S18). The motion analyzer 144 analyzes the values of the various running form parameters from the moving image and calculates the analysis value P by multiplying a length value by the conversion factor S (S20). The outputter 152 and the communicator 162 transmit the analysis result to the information terminal 12 (S21), and the evaluation processor 46 calculates the tentative value E for each of the various running form parameters by substituting the value V based on the physical condition as an explanatory variable into the regression equation for each parameter (S22) and conducts the evaluation based on whether the analysis value P for each parameter falls within the range of the tentative value E±the standard deviation SD (S24). The evaluation processor 46 retrieves the advice information associated with the evaluation result (S26), and the outputter 52 displays the result display screen generated by the screen generator 48 on the touch panel 60 (S30). According to the above-described configuration, it is also possible to easily improve the running form through image-analysis with a device that is widely available, such as a camera built in a smartphone, without using special equipment.

Third Embodiment

Figure 14:
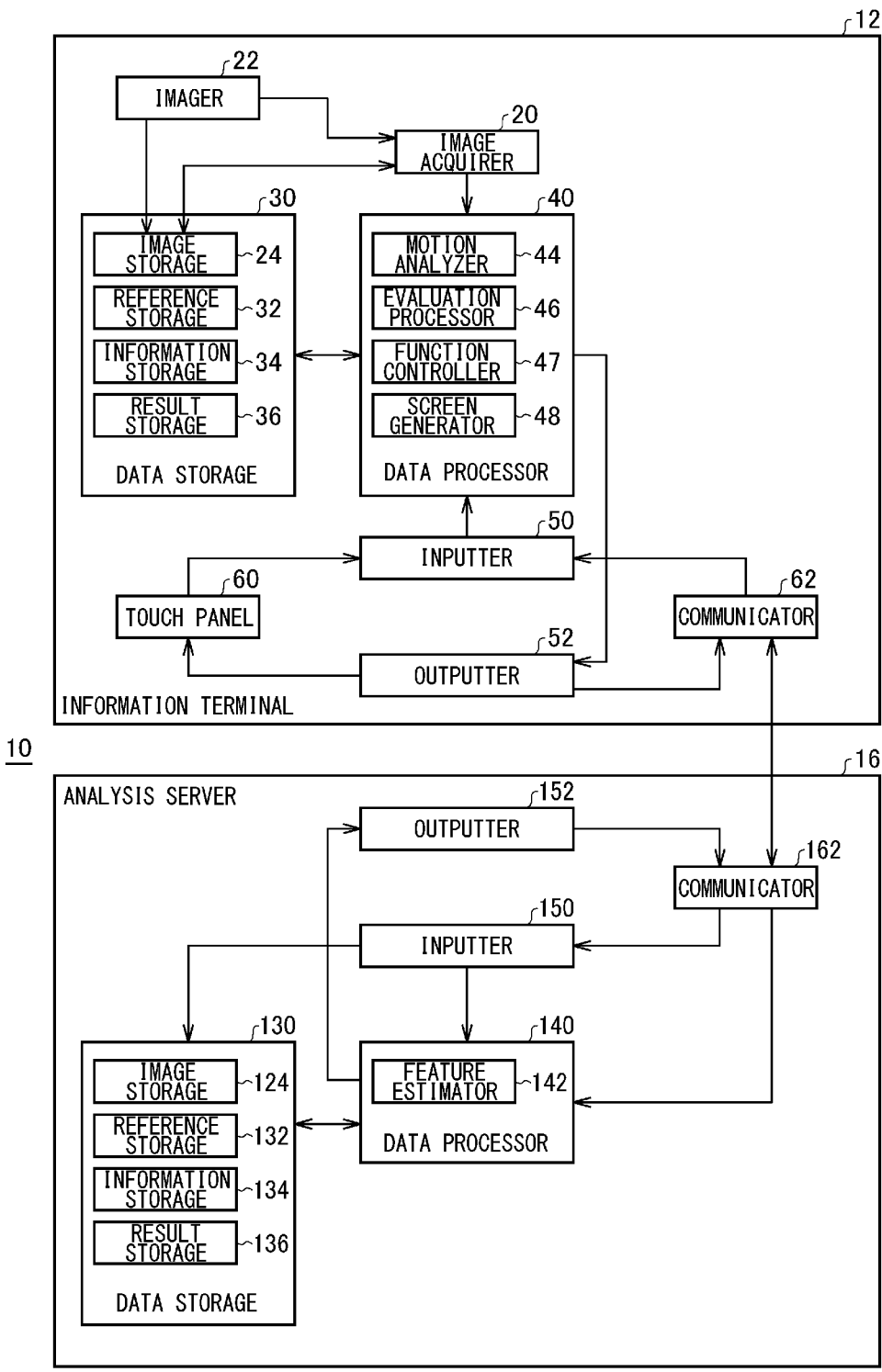
FIG. 14 is a functional block diagram showing basic structures of an information terminal and an analysis server according to a third embodiment.

FIG. 14 is a functional block diagram showing basic structures of an information terminal 12 and an analysis server 16 according to a third embodiment. A motion state evaluation system 10 according to the present embodiment is different from the motion state evaluation system 10 according to the first embodiment in that the motion state evaluation system 10 according to the present embodiment includes the information terminal 12 and the analysis server 16, and the "motion analyzer" and the "evaluation processor" are provided in the information terminal 12 rather than in a server (analysis server 16). Further, the motion state evaluation system 10 according to the present embodiment is different from the motion state evaluation system 10 according to the second embodiment in that the "motion analyzer" is provided in the information terminal 12 rather than in the server (analysis server 16). Hereinafter, a description will be given mainly of differences from the first embodiment and the second embodiment, and no description will be given of common points.

Coordinate data of the plurality of anatomical feature points estimated by the feature estimator 142 is transmitted to the information terminal 12 by the outputter 152 and the communicator 162. The reference storage 32 of the information terminal 12 prestores the height of the subject as the reference length. The data processor 40 includes the motion analyzer 44, the evaluation processor 46, the function controller 47, and the screen generator 48. The motion analyzer 44 obtains the height H on the image corresponding to the height of the subject based on the distance between predetermined joints estimated on the image from the coordinate data of the plurality of anatomical feature points. The motion analyzer 44 obtains a ratio of the height H on the image thus obtained to the height of the subject serving as the reference length prestored in the reference storage 32, and takes the ratio as the conversion factor S with which a distance on the image is converted into a distance in the metric system. The motion analyzer 44 analyzes the various running form parameters from the moving image and multiplies a length value by the conversion factor S to obtain the analysis value P of a corresponding running form parameter in the metric unit system in the real world.

The evaluation processor 46 calculates the tentative value E of each of the various running form parameters by substituting the value V based on the physical condition as an explanatory variable into the regression equation, and evaluates the motion of the subject based on whether a difference between the analysis value P calculated by the motion analyzer 44 and the tentative value E falls within the standard deviation. The analysis result and the evaluation result are stored in the result storage 36. The evaluation processor 46 retrieves the advice information associated with the result of the evaluation of the motion of the subject from the information storage 34. The advice information thus retrieved is displayed on the screen generated by the screen generator 48.

Figure 15:
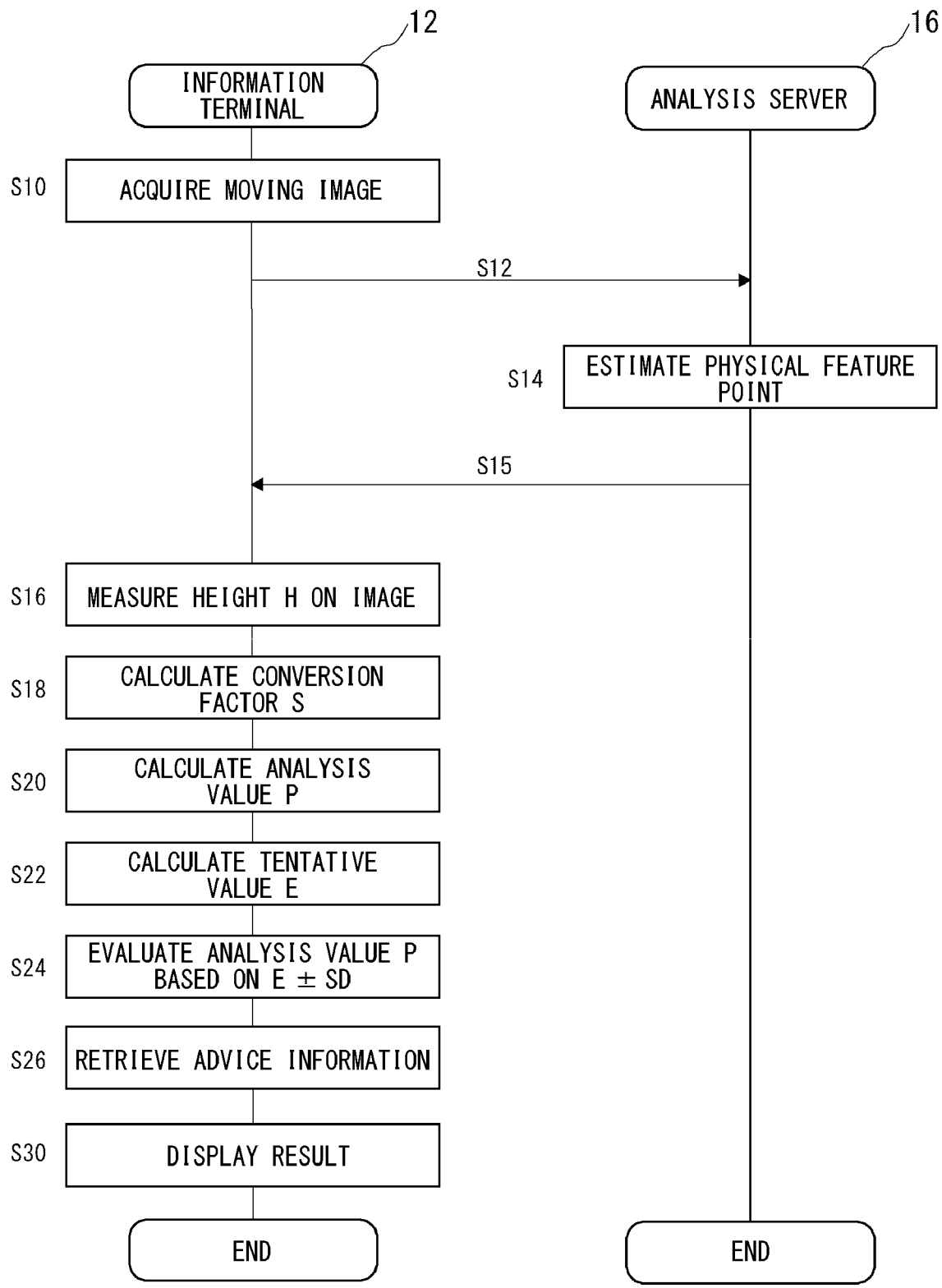
FIG. 15 is a flowchart showing a data flow between the information terminal and the analysis server, and a process of analyzing the moving image and conducting evaluation.

FIG. 15 is a flowchart showing a data flow between the information terminal 12 and the analysis server 16, and a process of analyzing the moving image and conducting evaluation. First, the image acquirer 20 acquires the moving image of the subject (S10), and the outputter 52 and the communicator 62 transfer the moving image to the analysis server 16 (S12). The feature estimator 142 estimates the plurality of anatomical feature points from the moving image thus received (S14). The outputter 152 and the communicator 162 transmit the coordinate data of the plurality of anatomical feature points to the information terminal 12 (S15), and the motion analyzer 44 measures the height H on the image (S16) and calculates the conversion factor S based on the ratio, to the prestored height of the subject, of the height H (S18). The motion analyzer 44 analyzes the values of the various running form parameters from the moving image and calculates the analysis value P by multiplying a length value by the conversion factor S (S20). The evaluation processor 46 calculates the tentative value E for each of the various running form parameters by substituting the value V based on the physical condition as an explanatory variable into the regression equation for each parameter (S22) and conducts the evaluation based on whether the analysis value P for each parameter falls within the range of the tentative value E±the standard deviation SD (S24). The evaluation processor 46 retrieves the advice information associated with the evaluation result (S26), and the outputter 52 displays the result display screen generated by the screen generator 48 on the touch panel 60 (S30). According to the above-described configuration, it is also possible to easily improve the running form through image-analysis with a device that is widely available, such as a camera built in a smartphone, without using special equipment.

Fourth Embodiment

Figure 16:
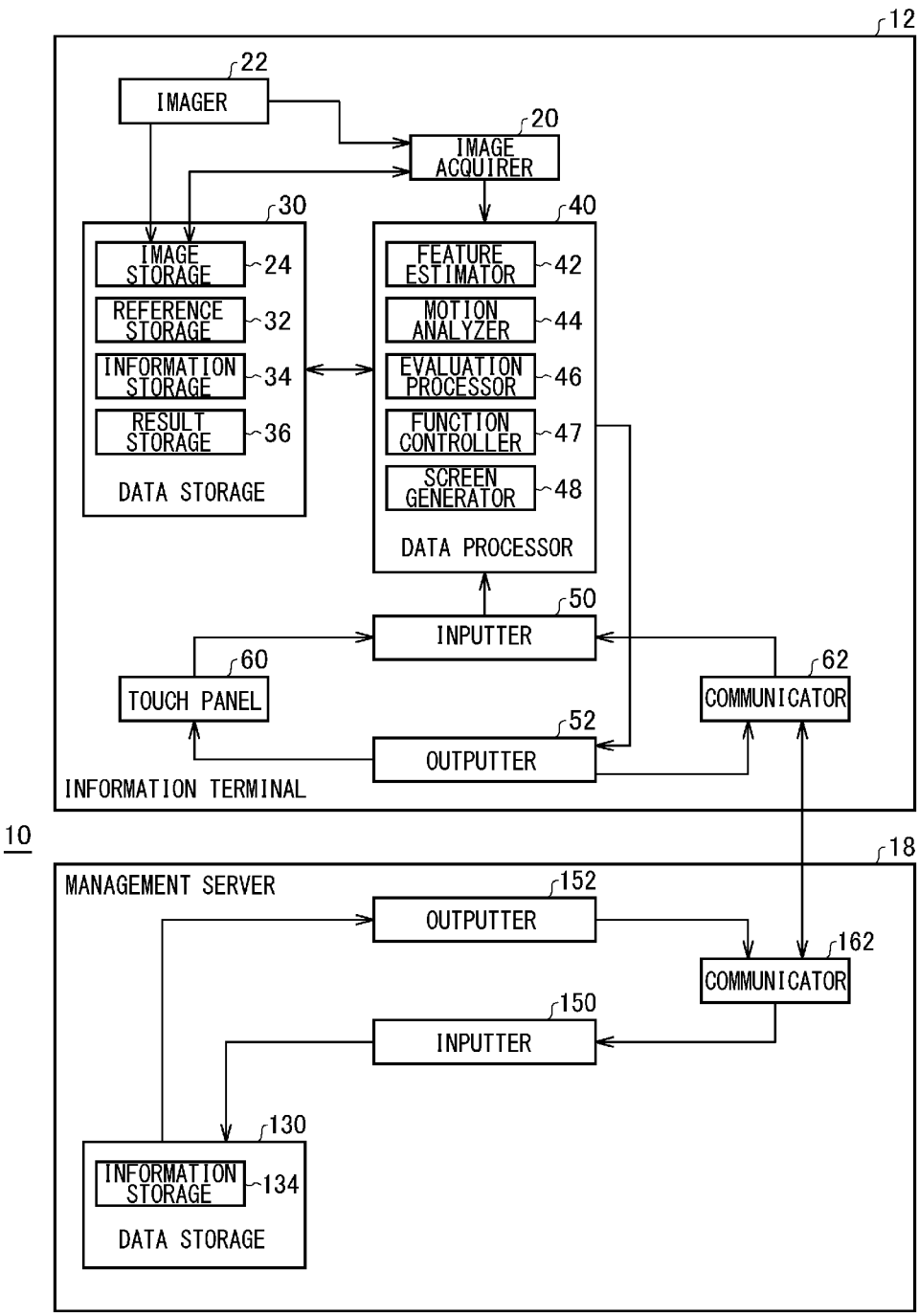
FIG. 16 is a functional block diagram showing basic structures of an information terminal and a management server according to a fourth embodiment.

FIG. 16 is a functional block diagram showing basic structures of an information terminal 12 and a management server 18 according to a fourth embodiment. A motion state evaluation system 10 according to the present embodiment is different from the motion state evaluation systems 10 according to the first to third embodiments in that the motion state evaluation system 10 according to the present embodiment includes the information terminal 12 and the management server 18, and the "feature estimator", the "motion analyzer" and the "evaluation processor" are provided in the information terminal 12 rather than in a server (management server 18). Hereinafter, a description will be given mainly of differences from the first to third embodiments, and no description will be given of common points.

According to the present embodiment, the moving image acquired by the image acquirer 20 is not transferred to the server (management server 18) as an analysis target, and analysis and evaluation are conducted in the information terminal 12. The data processor 40 includes the feature estimator 42, the motion analyzer 44, the evaluation processor 46, the function controller 47, and the screen generator 48. The feature estimator 42 estimates the plurality of anatomical feature points of the subject from the moving image. The motion analyzer 44 obtains the height H on the image corresponding to the height of the subject based on the distance between predetermined joints estimated on the image from the coordinate data of the plurality of anatomical feature points. The motion analyzer 44 obtains a ratio of the height H on the image thus obtained to the height of the subject serving as the reference length prestored in the reference storage 32, and takes the ratio as the conversion factor S with which a distance on the image is converted into a distance in the metric system. The motion analyzer 44 analyzes the various running form parameters from the moving image and multiplies a length value by the conversion factor S to obtain the analysis value P of a corresponding running form parameter in the metric unit system in the real world.

The evaluation processor 46 calculates the tentative value E of each of the various running form parameters by substituting the value V based on the physical condition as an explanatory variable into the regression equation, and evaluates the motion of the subject based on whether a difference between the analysis value P calculated by the motion analyzer 44 and the tentative value E falls within the standard deviation. The analysis result and the evaluation result are stored in the result storage 36. The evaluation processor 46 retrieves the advice information associated with the result of the evaluation of the motion of the subject from the information storage 34. The advice information thus retrieved is displayed on the screen generated by the screen generator 48.

The data storage 130 of the management server 18 includes the information storage 134. The information storage 134 stores the ID and password of the user, and when the function controller 47 logs in to the management server 18, verification is conducted using the ID and password stored in the information storage 134.

Figure 17:
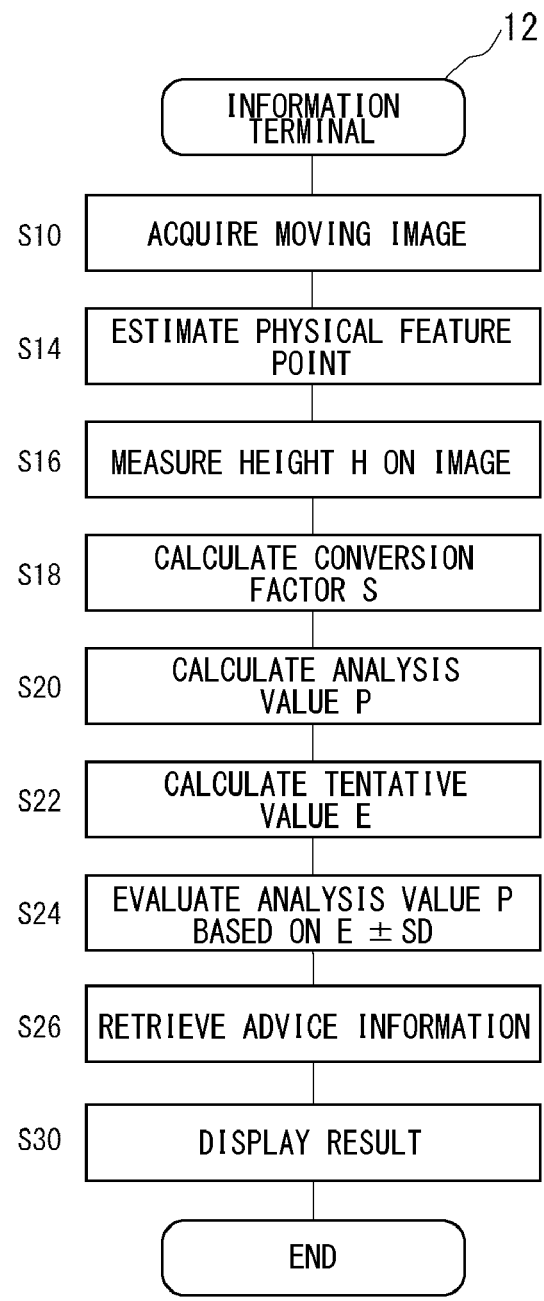
FIG. 17 is a flowchart showing a process of analyzing the moving image and conducting evaluation.

FIG. 17 is a flowchart showing a process of analyzing the moving image and conducting evaluation in the information terminal 12. First, the image acquirer 20 acquires the moving image of the subject (S10), the feature estimator 42 estimates the plurality of anatomical feature points from the moving image (S14), and the motion analyzer 44 measures the height H on the image (S16) and calculates the conversion factor S based on the ratio, to the prestored height of the subject, of the height H (S18). The motion analyzer 44 analyzes the values of the various running form parameters from the moving image and calculates the analysis value P by multiplying a length value by the conversion factor S (S20). The evaluation processor 46 calculates the tentative value E for each of the various running form parameters by substituting the value V based on the physical condition as an explanatory variable into the regression equation for each parameter (S22) and conducts the evaluation based on whether the analysis value P for each parameter falls within the range of the tentative value E±the standard deviation SD (S24). The evaluation processor 46 retrieves the advice information associated with the evaluation result (S26), and the outputter 52 displays the result display screen generated by the screen generator 48 on the touch panel 60 (S30).

According to the above-described configuration, it is also possible to easily improve the running form through image-analysis with a device that is widely available, such as a camera built in a smartphone, without using special equipment.

The present invention has been described based on the embodiments. It is to be understood by those skilled in the art that these embodiments are illustrative and that various modifications are possible for a combination of components or processes, and that such modifications are also within the scope of the present invention. Such modifications will be described below.

For each of the above-described embodiments, the description has been given of the example where the present invention is applied to analysis of a running form. On the other hand, according to each of the modification, the present invention may be applied to analysis of a walking form or analysis of forms in other sports. Example of the forms to be analyzed include a swing form in baseball or golf, a swimming form, and a ski form. The present invention is applied to not only forms in sports but also forms in arts such as dance and performance.

For each of the above-described embodiments, the description has been given of the example where the information on the height of the subject is used as the reference length. On the other hand, according to the modifications, a length of a body part other than the height may be used as the reference length. Alternatively, a moving image that captures the subject wearing an object having a predetermined length other than such a body part is taken, and the predetermined length may be taken as the reference length.

Any combination of the above-described embodiments and modifications is also useful as an embodiment of the present invention. A new embodiment resulting from such a combination exhibits the effect of each of the embodiments and modifications constituting the combination.

What is claimed is:

1. A motion state evaluation system comprising:
    an image acquirer configured to acquire a moving image of a subject;
    a feature estimator configured to estimate a plurality of anatomical feature points of the subject by a predetermined posture recognition method for performing image recognition to recognize a posture of the subject from the moving image;
    a reference storage configured to store a reference length that is an actual length of a predetermined reference part;
    a motion analyzer configured to obtain, as a value for use in evaluation of motion of the subject, a value representing a motion state of the subject from a distance on the image between the plurality of anatomical feature points based on a ratio, to the reference length, of a distance on the image that is determined from the plurality of anatomical feature points estimated and corresponds to the reference part; and
    an outputter configured to output the value representing the motion state.

2. The motion state evaluation system according to claim 1, wherein
    the feature estimator estimates a plurality of joint positions of the subject as the plurality of anatomical feature points, and
    the motion analyzer obtains the value representing the motion state of the subject based on a ratio, to the reference length, of a distance between predetermined joints estimated on the image.

3. The motion state evaluation system according to claim 1, wherein
    the reference storage stores a height of the subject as the reference length, and
    the motion analyzer obtains, as the value for use in evaluation of motion of the subject, the value representing the motion state of the subject from a feature point distance on the image of the plurality of anatomical feature points based on a ratio, to the height, of a distance on the image that is determined from the plurality of anatomical feature points and corresponds to the height of the subject.

4. The motion state evaluation system according to claim 2, wherein
    the reference storage stores a height of the subject as the reference length, and
    the motion analyzer obtains, as the value for use in evaluation of motion of the subject, the value representing the motion state of the subject from a feature point distance on the image of the plurality of anatomical feature points based on a ratio, to the height, of a distance on the image that is determined from the plurality of anatomical feature points and corresponds to the height of the subject.

5. The motion state evaluation system according to claim 1, further comprising an evaluation processor configured to evaluate the motion of the subject based on the value representing the motion state, wherein
    the value representing the motion state contains a value based on a width of predetermined motion of the subject during exercise,
    the reference storage further stores a regression equation and a standard deviation as a result of regression analysis between a value based on the width of the predetermined motion during exercise that is predetermined through analysis of moving images of a plurality of other subjects and a value based on a physical condition of the subject, the regression equation having the value based on the physical condition as an explanatory variable and the value based on the width of the predetermined motion as an objective variable,
    the evaluation processor calculates a tentative value of the value based on the width of the predetermined motion by substituting the value based on the physical condition of the subject into the regression equation, and evaluates the motion of the subject based on whether a difference between the value based on the width of the predetermined motion analyzed from the moving image of the subject and the tentative value falls within the standard deviation, and
    the outputter outputs a result of the evaluation.

6. The motion state evaluation system according to claim 2, further comprising an evaluation processor configured to evaluate the motion of the subject based on the value representing the motion state, wherein
    the value representing the motion state contains a value based on a width of predetermined motion of the subject during exercise,
    the reference storage further stores a regression equation and a standard deviation as a result of regression analysis between a value based on the width of the predetermined motion during exercise that is predetermined through analysis of moving images of a plurality of other subjects and a value based on a physical condition of the subject, the regression equation having the value based on the physical condition as an explanatory variable and the value based on the width of the predetermined motion as an objective variable, the evaluation processor calculates a tentative value of the value based on the width of the predetermined motion by substituting the value based on the physical condition of the subject into the regression equation, and evaluates the motion of the subject based on whether a difference between the value based on the width of the predetermined motion analyzed from the moving image of the subject and the tentative value falls within the standard deviation, and the outputter outputs a result of the evaluation.

7. The motion state evaluation system according to claim 3, further comprising an evaluation processor configured to evaluate the motion of the subject based on the value representing the motion state, wherein the value representing the motion state contains a value based on a width of predetermined motion of the subject during exercise, the reference storage further stores a regression equation and a standard deviation as a result of regression analysis between a value based on the width of the predetermined motion during exercise that is predetermined through analysis of moving images of a plurality of other subjects and a value based on a physical condition of the subject, the regression equation having the value based on the physical condition as an explanatory variable and the value based on the width of the predetermined motion as an objective variable, the evaluation processor calculates a tentative value of the value based on the width of the predetermined motion by substituting the value based on the physical condition of the subject into the regression equation, and evaluates the motion of the subject based on whether a difference between the value based on the width of the predetermined motion analyzed from the moving image of the subject and the tentative value falls within the standard deviation, and the outputter outputs a result of the evaluation.

8. The motion state evaluation system according to claim 4, further comprising an evaluation processor configured to evaluate the motion of the subject based on the value representing the motion state, wherein the value representing the motion state contains a value based on a width of predetermined motion of the subject during exercise, the reference storage further stores a regression equation and a standard deviation as a result of regression analysis between a value based on the width of the predetermined motion during exercise that is predetermined through analysis of moving images of a plurality of other subjects and a value based on a physical condition of the subject, the regression equation having the value based on the physical condition as an explanatory variable and the value based on the width of the predetermined motion as an objective variable, the evaluation processor calculates a tentative value of the value based on the width of the predetermined motion by substituting the value based on the physical condition of the subject into the regression equation, and evaluates the motion of the subject based on whether a difference between the value based on the width of the predetermined motion analyzed from the moving image of the subject and the tentative value falls within the standard deviation, and the outputter outputs a result of the evaluation.

9. The motion state evaluation system according to claim 5, further comprising an information storage configured to store advice information on the motion during exercise with the advice information and the result of the evaluation of the motion associated with each other, wherein the evaluation processor retrieves the advice information associated with the result of the evaluation of the motion of the subject from the information storage, and the outputter outputs the advice information retrieved.

10. The motion state evaluation system according to claim 6, further comprising an information storage configured to store advice information on the motion during exercise with the advice information and the result of the evaluation of the motion associated with each other, wherein the evaluation processor retrieves the advice information associated with the result of the evaluation of the motion of the subject from the information storage, and the outputter outputs the advice information retrieved.

11. The motion state evaluation system according to claim 7, further comprising an information storage configured to store advice information on the motion during exercise with the advice information and the result of the evaluation of the motion associated with each other, wherein the evaluation processor retrieves the advice information associated with the result of the evaluation of the motion of the subject from the information storage, and the outputter outputs the advice information retrieved.

12. The motion state evaluation system according to claim 8, further comprising an information storage configured to store advice information on the motion during exercise with the advice information and the result of the evaluation of the motion associated with each other, wherein the evaluation processor retrieves the advice information associated with the result of the evaluation of the motion of the subject from the information storage, and the outputter outputs the advice information retrieved.

13. A motion state evaluation device comprising:

an image acquirer configured to acquire a moving image of a subject;

a reference storage configured to store a reference length that is an actual length of a predetermined reference part;

a motion analyzer configured to obtain, as a value for use in evaluation of motion of the subject, a value representing a motion state of the subject from a distance on the image between the plurality of anatomical feature points based on a ratio, to the reference length, of a distance on the image that is determined from the plurality of anatomical feature points of the subject and corresponds to the reference part, the plurality of anatomical feature points being estimated by a predetermined posture recognition method for performing image recognition to recognize a posture of the subject from the moving image; and an outputter configured to display the value representing the motion state on a screen.

14. A motion state evaluation device comprising:

an image acquirer configured to acquire a moving image of a subject;

a feature estimator configured to estimate a plurality of anatomical feature points of the subject by a predetermined posture recognition method for performing image recognition to recognize a posture of the subject from the moving image;

a reference storage configured to store a reference length that is an actual length of a predetermined reference part;

a motion analyzer configured to obtain, as a value for use in evaluation of motion of the subject, a value representing a motion state of the subject from a distance on the image between the plurality of anatomical feature points based on a ratio, to the reference length, of a distance on the image that is determined from the plurality of anatomical feature points estimated and corresponds to the reference part; and an outputter configured to display the value representing the motion state on a screen.

15. A motion state evaluation server comprising:

a receiver configured to receive a moving image of a subject from a predetermined information terminal over a network;

a feature estimator configured to estimate a plurality of anatomical feature points of the subject by a predetermined posture recognition method for performing image recognition to recognize a posture of the subject from the moving image;

a reference storage configured to store a reference length that is an actual length of a predetermined reference part;

a motion analyzer configured to obtain, as a value for use in evaluation of motion of the subject, a value representing a motion state of the subject from a distance on the image between the plurality of anatomical feature points based on a ratio, to the reference length, of a distance on the image that is determined from the plurality of anatomical feature points estimated and corresponds to the reference part; and an outputter configured to output the value representing the motion state.

16. A motion state evaluation method comprising:

acquiring a moving image of a subject;

estimating a plurality of anatomical feature points of the subject by a predetermined posture recognition method for performing image recognition to recognize a posture of the subject from the moving image;

obtaining, as a value for use in evaluation of motion of the subject, a value representing a motion state of the subject from a distance on the image between the plurality of anatomical feature points based on a ratio, to a reference length that is a prestored actual length of a predetermined reference part, of a distance on the image that is determined from the plurality of anatomical feature points estimated and corresponds to the reference part; and outputting the value representing the motion state.

17. A non-transitory computer-readable storage medium storing a motion state evaluation program for causing a computer having a memory and a processor to execute processing, the processing comprising:

acquiring a moving image of a subject with a predetermined imaging means;

transmitting the moving image to a predetermined server over a network;

receiving a value representing a motion state of the subject over the network, the value being obtained, based on a ratio, to a reference length that is a prestored actual length of a predetermined reference part, of a distance on the image that is determined from a plurality of anatomical feature points of the subject estimated by a predetermined posture recognition method for performing image recognition to recognize a posture of the subject from the moving image in the server and corresponds to the reference part, from a distance on the image between the plurality of anatomical feature points, and displaying the value representing the motion state on a screen.

18. A non-transitory computer-readable storage medium storing a motion state evaluation program for causing a computer having a memory and a processor to execute processing, the processing comprising:

acquiring a moving image of a subject with a predetermined imaging means;

causing the processor to estimate a plurality of anatomical feature points of the subject by a predetermined posture recognition method for performing image recognition to recognize a posture of the subject from the moving image;

retrieving a reference length that is an actual length of a predetermined reference part from a predetermined storage medium;

causing the processor to obtain, as a value for use in evaluation of motion of the subject, a value representing a motion state of the subject from a distance on the image between the plurality of anatomical feature points based on a ratio, to the reference length, of a distance on the image that is determined from the plurality of anatomical feature points estimated and corresponds to the reference part; and displaying the value representing the motion state on a screen.

* * * * *